United States Patent
Dachs, II et al.

(10) Patent No.: US 11,660,152 B2
(45) Date of Patent: May 30, 2023

(54) MOTOR INTERFACE FOR PARALLEL DRIVE SHAFTS WITHIN AN INDEPENDENTLY ROTATING MEMBER

(71) Applicant: Intuitive Surgical Operations, Inc., Sunnyvale, CA (US)

(72) Inventors: Gregory W. Dachs, II, San Francisco, CA (US); Todd E. Murphy, Palo Alto, CA (US); William A. Burbank, Sandy Hook, CT (US); William A. McDonald, II, Santa Clara, CA (US); Bruce Michael Schena, Menlo Park, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 456 days.

(21) Appl. No.: 16/998,838

(22) Filed: Aug. 20, 2020

(65) Prior Publication Data
US 2020/0382921 A1 Dec. 3, 2020

Related U.S. Application Data

(60) Continuation of application No. 15/677,752, filed on Aug. 15, 2017, now Pat. No. 10,798,540, which is a
(Continued)

(51) Int. Cl.
*A61B 34/30* (2016.01)
*A61B 17/072* (2006.01)
(Continued)

(52) U.S. Cl.
CPC ........ *A61B 34/30* (2016.02); *A61B 17/07207* (2013.01); *A61B 34/71* (2016.02);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS

| | | |
|---|---|---|
| 61,581 A | 1/1867 | Taylors et al. |
| 76,819 A | 4/1868 | Ross et al. |

(Continued)

FOREIGN PATENT DOCUMENTS

| | | |
|---|---|---|
| CN | 1457747 A | 11/2003 |
| CN | 1534213 A | 10/2004 |

(Continued)

OTHER PUBLICATIONS

Extended European Search Report for Application No. EP20187989.7 dated Dec. 4, 2020, 08 pages.

(Continued)

*Primary Examiner* — Scott A Smith
(74) *Attorney, Agent, or Firm* — Kilpatrick Townsend & Stockton LLP

(57) ABSTRACT

Minimally invasive surgical methods employ an offset drive shaft to actuate an end effector. A minimally invasive surgical method includes introducing an end effector to an internal surgical site. The end effector includes an end effector base that is coupled to the instrument shaft via a wrist. An end effector articulation mechanism is operated to reorient the end effector base relative to the instrument shaft. A surgical task is performed by operating a motor to rotate an offset drive shaft relative to the instrument shaft to actuate the end effector.

20 Claims, 18 Drawing Sheets

Related U.S. Application Data division of application No. 14/144,510, filed on Dec. 30, 2013, now Pat. No. 9,763,740, which is a division of application No. 12/945,461, filed on Nov. 12, 2010, now Pat. No. 8,640,788.

(60) Provisional application No. 61/260,919, filed on Nov. 13, 2009.

(51) Int. Cl.
    *A61B 34/00*      (2016.01)
    *A61B 17/00*      (2006.01)
    *H04W 84/12*      (2009.01)
    *A61B 17/29*      (2006.01)
    *A61B 17/068*      (2006.01)
    *A61B 17/115*      (2006.01)

(52) U.S. Cl.
CPC ........... *A61B 17/068* (2013.01); *A61B 17/072* (2013.01); *A61B 17/115* (2013.01); *A61B 2017/00477* (2013.01); *A61B 2017/07214* (2013.01); *A61B 2017/2902* (2013.01); *A61B 2017/2927* (2013.01); *A61B 2034/302* (2016.02); *H04W 84/12* (2013.01)

(58) Field of Classification Search
CPC ........... A61B 2017/00477; A61B 2017/00022; A61B 2017/00398; A61B 2017/07214; A61B 2017/07228; A61B 2017/2902; A61B 2017/2927; A61B 34/30; A61B 34/31; A61B 34/71; A61B 34/76
USPC ........ 227/19, 175.1, 176.1; 606/1, 139, 205, 606/219
See application file for complete search history.

(56) References Cited

U.S. PATENT DOCUMENTS

| | | | |
|---|---|---|---|
| 1,665,241 A | 4/1928 | Weiss |
| 2,067,286 A | 1/1937 | Pearce |
| 2,297,457 A | 9/1942 | Josef |
| 2,302,599 A | 11/1942 | Burney |
| 2,687,025 A | 8/1954 | Ernest |
| 3,017,755 A | 1/1962 | Miller |
| 3,324,683 A | 6/1967 | Schroter |
| 3,720,954 A | 3/1973 | Czyryk |
| 3,747,368 A | 7/1973 | Morin |
| 3,857,256 A | 12/1974 | Girguis et al. |
| 3,906,747 A | 9/1975 | Orain |
| 3,940,946 A | 3/1976 | Andersen |
| 4,606,695 A | 8/1986 | Lenz |
| 4,642,021 A | 2/1987 | Kikuchi |
| 4,686,866 A | 8/1987 | Rosheim |
| 4,790,225 A | 12/1988 | Moody et al. |
| 4,799,817 A | 1/1989 | Geisthoff |
| 4,892,300 A | 1/1990 | Svyatsky |
| 4,911,033 A | 3/1990 | Rosheim et al. |
| 4,969,533 A | 11/1990 | Holm et al. |
| 5,062,761 A | 11/1991 | Glachet |
| 5,069,569 A | 12/1991 | Lieser |
| 5,101,681 A | 4/1992 | Shpigel |
| 5,314,466 A | 5/1994 | Stern et al. |
| 5,507,773 A | 4/1996 | Huitema et al. |
| 5,710,870 A | 1/1998 | Ohm et al. |
| 5,740,699 A | 4/1998 | Ballantyne et al. |
| 5,792,135 A | 8/1998 | Madhani et al. |
| 5,797,900 A | 8/1998 | Madhani et al. |
| 5,807,377 A | 9/1998 | Madhani et al. |
| 5,828,813 A | 10/1998 | Ohm |
| 5,887,778 A | 3/1999 | Maurer et al. |
| 5,954,259 A | 9/1999 | Viola et al. |
| 6,010,054 A | 1/2000 | Johnson et al. |
| 6,394,998 B1 | 5/2002 | Wallace et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,817,974 B2 | 11/2004 | Cooper et al. |
| 6,860,860 B2 | 3/2005 | Viola |
| 6,969,385 B2 | 11/2005 | Moreyra |
| 7,066,926 B2 | 6/2006 | Wallace et al. |
| 7,086,926 B2 | 8/2006 | Falla |
| 7,121,781 B2 | 10/2006 | Sanchez |
| 7,320,700 B2 | 1/2008 | Cooper et al. |
| 7,464,846 B2 | 12/2008 | Shelton et al. |
| 7,485,127 B2 | 2/2009 | Nistal |
| 7,641,671 B2 | 1/2010 | Crainich |
| 7,708,758 B2 | 5/2010 | Lee et al. |
| 7,918,230 B2 | 4/2011 | Whitman et al. |
| 8,640,788 B2 | 2/2014 | Dachs, II et al. |
| 8,852,174 B2 | 10/2014 | Burbank |
| 8,876,857 B2 | 11/2014 | Burbank |
| 9,101,381 B2 | 8/2015 | Burbank et al. |
| 9,226,761 B2 | 1/2016 | Burbank |
| 9,259,275 B2 | 2/2016 | Burbank |
| 9,763,740 B2 | 9/2017 | Dachs, II et al. |
| 10,045,823 B2 | 8/2018 | Burbank |
| 10,098,635 B2 | 10/2018 | Burbank |
| 10,206,748 B2 | 2/2019 | Burbank |
| 10,292,767 B2 | 5/2019 | Burbank et al. |
| 10,779,896 B2 | 9/2020 | Dachs, II et al. |
| 10,835,331 B2 | 11/2020 | Burbank |
| 10,898,188 B2 | 1/2021 | Burbank |
| 11,083,458 B2* | 8/2021 | Harris ............... A61B 17/07207 |
| 11,090,119 B2 | 8/2021 | Burbank |
| 11,291,447 B2* | 4/2022 | Shelton, IV ...... A61B 17/07207 |
| 11,304,696 B2* | 4/2022 | Shelton, IV ...... A61B 17/07207 |
| 11,304,768 B2 | 4/2022 | Burbank |
| 11,317,917 B2* | 5/2022 | Shelton, IV .......... A61B 17/072 |
| 11,357,572 B2 | 6/2022 | Burbank et al. |
| 11,452,526 B2* | 9/2022 | Ross .................... A61B 17/072 |
| 11,523,859 B2* | 12/2022 | Shelton, IV ........... A61B 34/37 |
| 2001/0021859 A1 | 9/2001 | Kawai et al. |
| 2001/0023311 A1 | 9/2001 | Snow |
| 2002/0120265 A1 | 8/2002 | Fowler |
| 2002/0143346 A1 | 10/2002 | McGuckin, Jr. et al. |
| 2002/0188299 A1 | 12/2002 | Reiley et al. |
| 2003/0105478 A1 | 6/2003 | Whitman et al. |
| 2003/0114851 A1 | 6/2003 | Truckai et al. |
| 2003/0130677 A1 | 7/2003 | Whitman et al. |
| 2003/0158576 A1 | 8/2003 | Nagase et al. |
| 2003/0192391 A1 | 10/2003 | Uematsu et al. |
| 2003/0216667 A1 | 11/2003 | Viola |
| 2004/0011576 A1 | 1/2004 | Taniguchi et al. |
| 2004/0018909 A1 | 1/2004 | Hwa et al. |
| 2004/0193146 A1 | 9/2004 | Lee et al. |
| 2004/0260334 A1 | 12/2004 | Braun |
| 2005/0015356 A1 | 1/2005 | Ireland et al. |
| 2005/0043717 A1 | 2/2005 | Snow |
| 2005/0075664 A1 | 4/2005 | Nagase et al. |
| 2005/0163560 A1 | 7/2005 | Chene et al. |
| 2006/0048787 A1 | 3/2006 | Manzo et al. |
| 2006/0074415 A1 | 4/2006 | Scott et al. |
| 2006/0079884 A1 | 4/2006 | Manzo et al. |
| 2006/0089202 A1 | 4/2006 | Losi, Jr. |
| 2006/0111209 A1 | 5/2006 | Hinman et al. |
| 2006/0111210 A1 | 5/2006 | Hinman |
| 2006/0137888 A1 | 6/2006 | Soika et al. |
| 2006/0199999 A1 | 9/2006 | Ikeda et al. |
| 2007/0021738 A1 | 1/2007 | Hasser et al. |
| 2007/0023477 A1 | 2/2007 | Whitman et al. |
| 2007/0055219 A1 | 3/2007 | Whitman et al. |
| 2007/0221700 A1 | 9/2007 | Ortiz et al. |
| 2007/0233052 A1 | 10/2007 | Brock |
| 2008/0039256 A1 | 2/2008 | Jinno et al. |
| 2008/0058776 A1 | 3/2008 | Jo et al. |
| 2008/0177283 A1 | 7/2008 | Lee et al. |
| 2008/0257935 A1 | 10/2008 | Viola et al. |
| 2008/0271906 A1 | 11/2008 | Walker |
| 2008/0312668 A1 | 12/2008 | Grace |
| 2009/0047061 A1 | 2/2009 | Chene et al. |
| 2009/0065549 A1 | 3/2009 | Viola |
| 2009/0090764 A1 | 4/2009 | Viola et al. |

(56) References Cited

U.S. PATENT DOCUMENTS

| | | | |
|---|---|---|---|
| 2009/0112229 A1 | 4/2009 | Omori et al. | |
| 2009/0173178 A1 | 7/2009 | Okazaki | |
| 2009/0183887 A1 | 7/2009 | Baber et al. | |
| 2009/0192519 A1 | 7/2009 | Omori | |
| 2009/0198253 A1 | 8/2009 | Omori | |
| 2009/0264931 A1 | 10/2009 | Miller et al. | |
| 2010/0011900 A1 | 1/2010 | Burbank et al. | |
| 2010/0011901 A1 | 1/2010 | Burbank | |
| 2010/0016852 A1 | 1/2010 | Manzo et al. | |
| 2010/0016853 A1 | 1/2010 | Burbank | |
| 2011/0118708 A1 | 5/2011 | Burbank et al. | |
| 2011/0152879 A1 | 6/2011 | Williams et al. | |
| 2017/0367775 A1 | 12/2017 | Dachs, II et al. | |
| 2018/0318015 A1 | 11/2018 | Burbank et al. | |
| 2019/0021733 A1 | 1/2019 | Burbank et al. | |
| 2019/0099231 A1* | 4/2019 | Bruehwiler | A61B 17/29 |
| 2019/0216551 A1 | 7/2019 | Burbank | |
| 2019/0298453 A1 | 10/2019 | Burbank et al. | |
| 2021/0022813 A1 | 1/2021 | Burbank | |
| 2021/0106330 A1 | 4/2021 | Burbank | |
| 2021/0338332 A1 | 11/2021 | Burbank | |

FOREIGN PATENT DOCUMENTS

| | | |
|---|---|---|
| CN | 101365391 A | 2/2009 |
| CN | 101495046 A | 7/2009 |
| EP | 0710089 B1 | 12/2001 |
| EP | 1782927 A2 | 5/2007 |
| EP | 1813200 A2 | 8/2007 |
| EP | 2036505 B1 | 11/2010 |
| EP | 2263568 A2 | 12/2010 |
| EP | 1585425 B1 | 8/2016 |
| FR | 38899 E | 8/1931 |
| FR | 1012165 A | 7/1952 |
| GB | 195353 A | 3/1924 |
| GB | 802506 A | 10/1958 |
| GB | 2294526 A | 5/1996 |
| JP | 58217823 A | 12/1983 |
| JP | H03501233 A | 3/1991 |
| JP | H07163574 A | 6/1995 |
| JP | 2000023996 A | 1/2000 |
| JP | 2001276091 A | 10/2001 |
| JP | 2002306496 A | 10/2002 |
| JP | 2005505309 A | 2/2005 |
| JP | 2006075376 A | 3/2006 |
| JP | 2007038003 A | 2/2007 |
| JP | 2007130471 A | 5/2007 |
| JP | 2007524451 A | 8/2007 |
| JP | 2008036219 A | 2/2008 |
| JP | 2009502352 A | 1/2009 |
| JP | 2009066400 A | 4/2009 |
| JP | 2009112538 A | 5/2009 |
| JP | 2009165504 A | 7/2009 |
| JP | 2009178230 A | 8/2009 |
| JP | 2009178506 A | 8/2009 |
| JP | 2010540041 A | 12/2010 |
| WO | WO-8902544 A1 | 3/1989 |
| WO | WO-9743942 A1 | 11/1997 |
| WO | WO-9743943 A1 | 11/1997 |
| WO | WO-03001987 A2 | 1/2003 |
| WO | WO-2006073581 A2 | 7/2006 |
| WO | WO-2006075153 A1 | 7/2006 |
| WO | WO-2007120353 A2 | 10/2007 |
| WO | WO-2007146987 A2 | 12/2007 |
| WO | WO-2009039506 A1 | 3/2009 |
| WO | WO-2009126955 A2 | 10/2009 |
| WO | WO-2011060315 A2 | 5/2011 |

OTHER PUBLICATIONS

Communication Pursuant to Article 94(3) EPC dated Jul. 12, 2013 for European Application No. 10781556.5 filed Nov. 12, 2010.
Communication Pursuant to Article 94(3) EPC dated Dec. 20, 2013 for European Application No. 10779428.1 filed Nov. 12, 2010.
Extended European Search Report for Application No. EP19203804 dated Feb. 3, 2020, 7 pages.
Extended European Search Report for Application No. 12162263.3, dated Oct. 26, 2016, 7 pages.
Extended European Search Report for Application No. 12162273.2, dated Oct. 26, 2016, 7 pages.
Extended European Search Report for Application No. 13151922.5, dated Oct. 26, 2016, 7 pages.
Extended European Search Report for Application No. 18171951.9, dated Aug. 7, 2018, 7 pages.
Extended European Search Report for Application No. 18198026.9, dated Dec. 3, 2018, 8 pages.
Extended European Search Report for Application No. EP18170942. 9, dated Aug. 6, 2018, 9 pages.
Extended European Search Report for Application No. EP19206336 dated Feb. 11, 2020, 9 pages.
Office Action dated Jul. 2, 2014 for Chinese Application No. 201080051475.3 filed Nov. 12, 2010.
Office Action dated May 2, 2014 for Japanese Application No. 2012539033 filed Nov. 12, 2010.
Office Action dated May 8, 2014 for Japanese Application No. 2012539037 filed Nov. 12, 2010.
Office Action dated Aug. 13, 2014 for Japanese Application No. 2012539035 filed Nov. 13, 2009.
Office Action dated Jun. 17, 2015 for Japanese Application No. 2013200054 filed Sep. 26, 2013, 10 pages.
Office Action dated Aug. 26, 2014 for Japanese Application No. 2013200054 filed Sep. 26, 2013.
Office Action dated Aug. 29, 2014 for Japanese Application No. 2013200053 filed Sep. 26, 2013.
Office Action dated May 6, 2014 for Chinese Application No. 201080051059.3 filed Nov. 12, 2010.
PCT/US10/56601 International Search Report and Written Opinion of the International Searching Authority, dated Jul. 6, 2011, 18 pages.
PCT/US10/56607 Invitation to Pay Additional Fees and Results of the Partial International Search, dated Mar. 21, 2011, 5 pages.
PCT/US10/56610 International Search Report and Written Opinion of the International Searching Authority, dated Feb. 18, 2011, 16 pages.
PCT/US2010/056607 International Search Report and Written Opinion of the International Searching Authority, dated Jun. 15, 2011, 20 pages.
Rosheim, Mark E., Chapter 5: "Pitch-Yaw-Roll Wrists," Robot Wrist Actuators, Wiley & Sons, New York, 1989, pp. 95-206.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP22170371. 3, dated Jul. 29.2022, 09 pages.

* cited by examiner

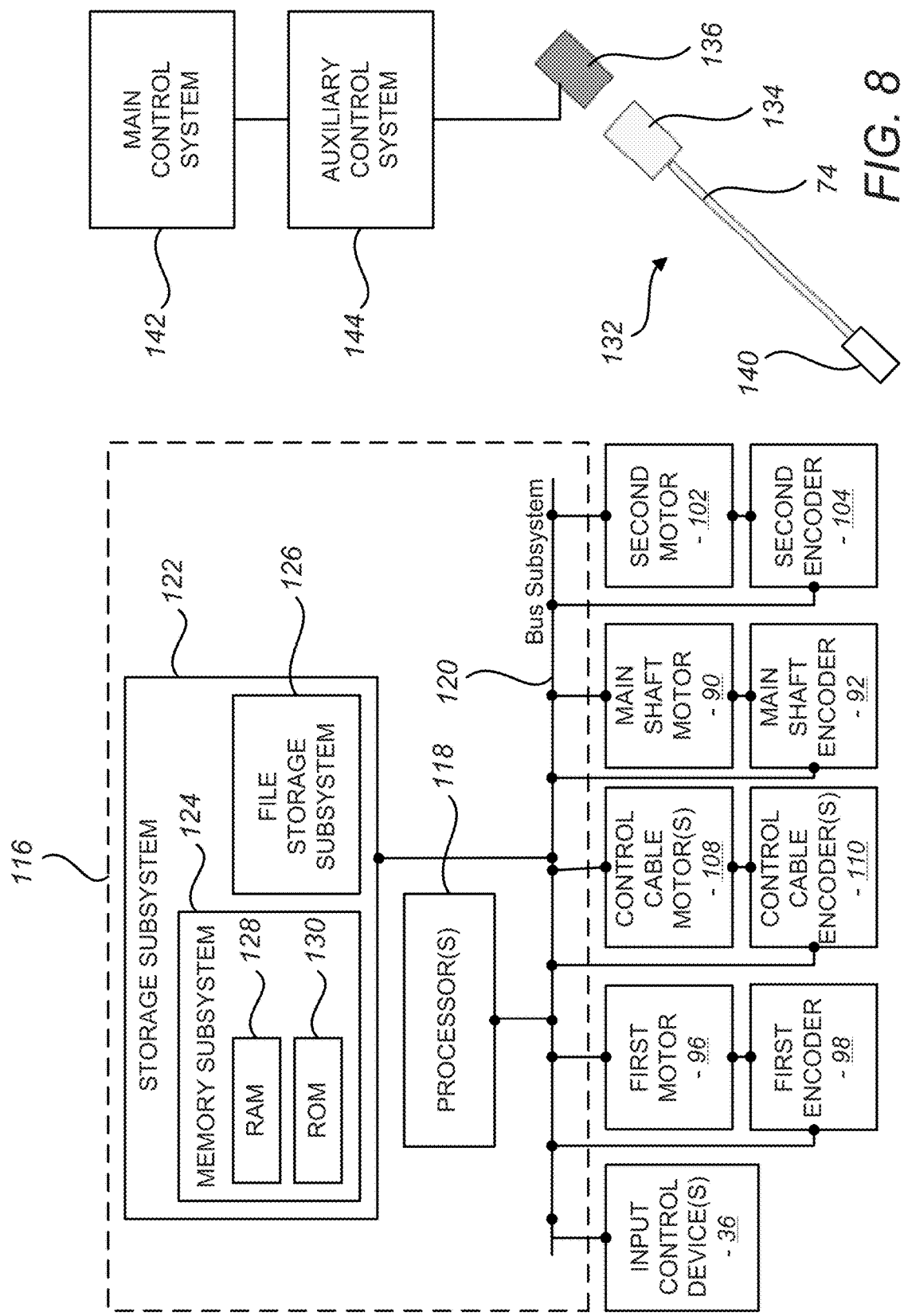

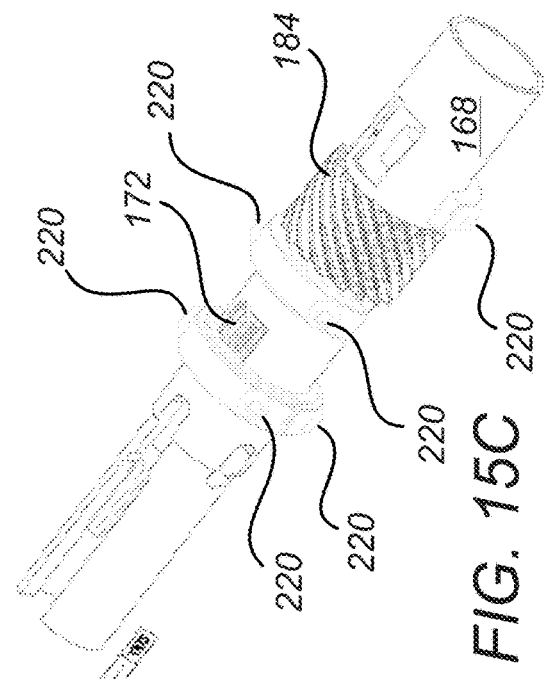
FIG. 15C
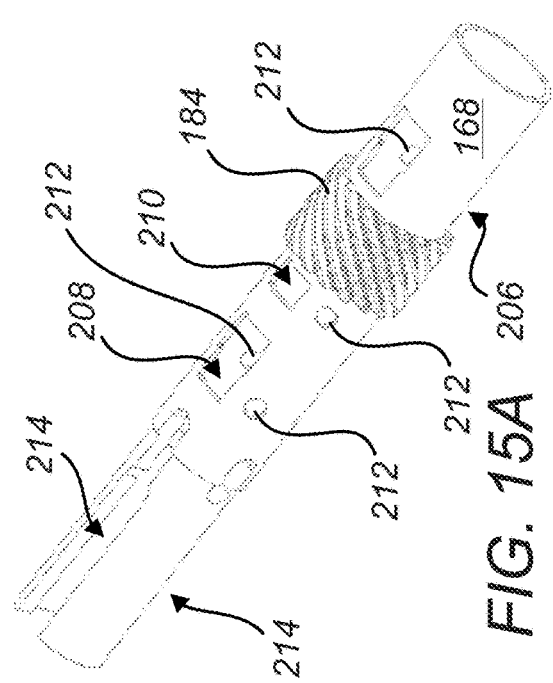
FIG. 15A
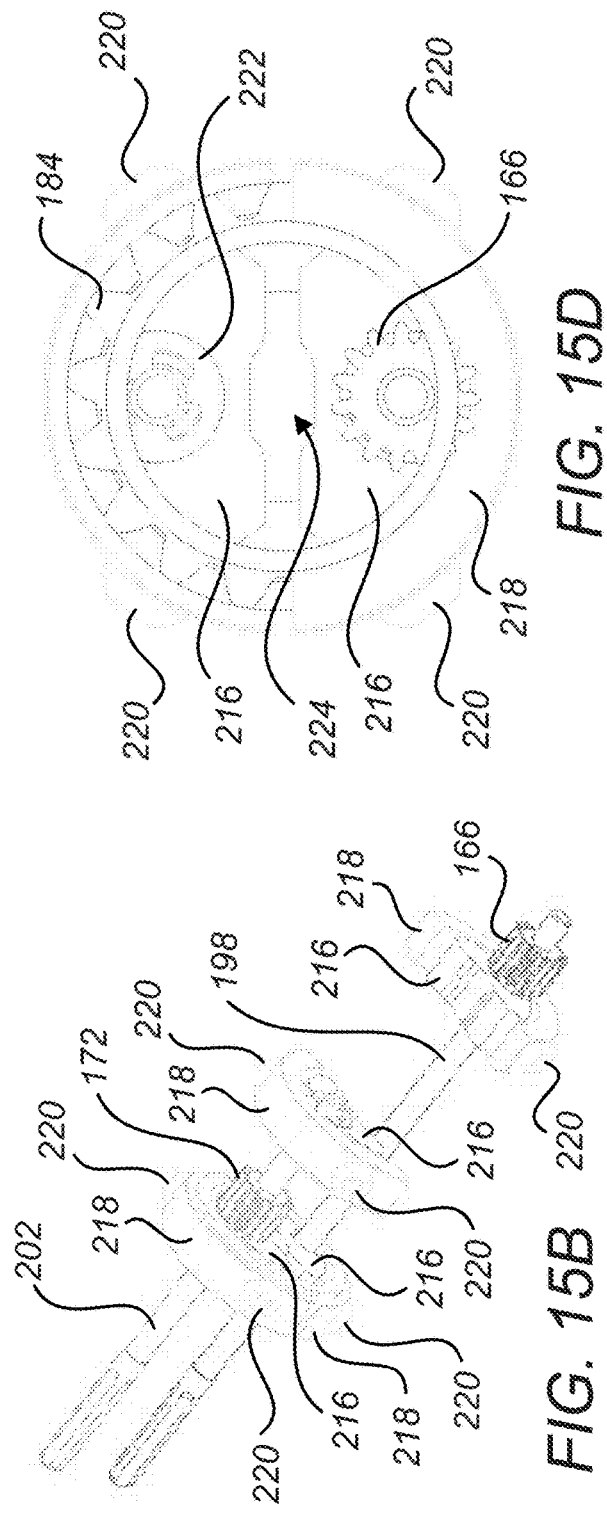
FIG. 15D
FIG. 15B

MOTOR INTERFACE FOR PARALLEL DRIVE SHAFTS WITHIN AN INDEPENDENTLY ROTATING MEMBER

CROSS-REFERENCES TO RELATED APPLICATIONS

The present application is a Continuation of U.S. Ser. No. 15/677,782 filed Aug. 15, 2017 (now U.S. Pat. No. 10,779, 896); which is a Divisional of U.S. Ser. No. 14/144,510 filed Dec. 30, 2013 (now U.S. Pat. No. 9,763,740); which is a Divisional of U.S. Ser. No. 12/945,461 filed Nov. 12, 2010 (now U.S. Pat. No. 8,640,788); which claims the benefit of U.S. Provisional Appln Ser. No. 61/260,919 filed Nov. 13, 2009; the full disclosures which are incorporated herein by reference in their entirety for all purposes.

The present application is also related to U.S. Ser. No. 12/945,730 filed Nov. 12, 2010 (now U.S. Pat. No. 9,259, 275); U.S. Ser. No. 12/945,740 filed Nov. 12, 2010; U.S. Ser. No. 12/945,748 filed Nov. 12, 2010 (now U.S. Pat. No. 8,852,174); and U.S. Ser. No. 12/945,541 filed Nov. 12, 2010 (now U.S. Pat. No. 8,876,857); the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Non robotic linear clamping, cutting and stapling devices have been employed in many different surgical procedures. For example, such a device can be used to resect a cancerous or anomalous tissue from a gastro-intestinal tract. Unfortunately, many known surgical devices, including known linear clamping, cutting and stapling devices, often have opposing jaws that may be difficult to maneuver within a patient. For known devices having opposing jaws that are maneuverable within a patient, such devices may not generate sufficient clamping force for some surgical applications (e.g., tissue clamping, tissue stapling, tissue cutting, etc.), which may reduce the effectiveness of the surgical device.

Thus, there is believed to be a need for an improvement in the maneuverability of surgical end effectors, particularly with regard to minimally invasive surgery. In addition, there is believed to be a need for surgical end effectors with high actuation force, for example, high clamping force.

BRIEF SUMMARY

Mechanisms, assemblies, systems, tools, and methods are provided, many of which incorporate the use of an offset drive shaft within an independently rotating member. Such mechanisms, assemblies, systems, tools, and methods may be particularly beneficial for use in surgery, for example, in minimally invasive surgery, in minimally invasive robotic surgery, as well as other types of surgery. The combination of an offset drive shaft mounted for rotation within an independently rotatable instrument shaft allows significant actuation power to be transferred to an end effector while leaving a central region of the instrument shaft available for routing of other components, for example, control cables, control wires, catheters, or other such components. Drive shaft actuation can be used to articulate and/or orient an end effector, for example, so as to provide a relatively high desired clamping force, such as for cutting or stapling, optionally with a limited response rate. Cable actuation may be used for relatively lower force articulation and/or orientation of the end effector when a higher response rate is desired, such as when telesurgically grasping and manipulating tissues. Exemplary hybrid cable/shaft actuated systems may selectably actuate a single grasping/treatment jaw joint using either a high force shaft drive or a high response cable drive. While the various embodiments disclosed herein are primarily described with regard to surgical applications, related mechanisms, assemblies, systems, tools, and methods may find use in a wide variety of applications, both inside and outside a human body, as well as in non-surgical applications.

In a first aspect, a mechanism including an offset drive shaft mounted within a rotating main shaft is provided. The mechanism includes a base, a main shaft mounted to rotate relative to the base, a first drive shaft mounted inside the main shaft, and a first drive feature engaged with the first drive shaft. The main shaft includes a proximal end, a distal end, and a main shaft rotational axis defined therebetween. The first drive shaft is offset from the main shaft rotational axis. A first drive feature rotational axis is defined for the first drive feature and is fixed relative to the base as the main shaft rotates. The first drive feature rotates the first drive shaft.

Various approaches may be used to rotate the first drive shaft via the first drive feature. For example, the main shaft rotational axis and the first drive feature rotational axis can be coincident. Engagement between the first drive feature and the first drive shaft can permit an axial movement of the first drive shaft relative to the base. The first drive feature can be engaged with the first drive shaft through an opening in the main shaft. The first drive shaft can include a second drive feature that protrudes through the main shaft opening and engages the first drive feature. The second drive feature can include external gear teeth. The first drive feature can include an internal ring gear.

In many embodiments, the mechanism includes a third drive feature for rotating the main shaft. For example, a third drive feature having a third drive feature rotational axis can engage the main shaft. The third drive feature rotational axis can be fixed relative to the base as the third drive feature rotates the main shaft.

In many embodiments, a second drive shaft is mounted inside the main shaft and offset from the main shaft rotational axis. A fourth drive feature having a fourth drive feature rotational axis can be engaged with the second drive shaft. A fourth drive feature rotational axis can be fixed relative to the base as the main shaft rotates. The fourth drive feature can rotate the second drive shaft. The fourth drive feature can be engaged with the second drive shaft through an opening in the main shaft.

In many embodiments, the support of the first drive shaft is integrated into the main shaft. For example, the main shaft can include a recess configured to interface with a bearing supporting the first drive shaft, and the mechanism can further include the bearing supporting the first drive shaft. The mechanism can further include a retaining ring to retain the bearing supporting the first drive shaft.

In many embodiments, an end effector is coupled with the distal end of the main shaft. The end effector can be coupled with the first drive shaft and/or with the second drive shaft. The end effector can be rotated by a rotation of the main shaft. A rotation of the first drive shaft and/or of the second drive shaft can actuate the end effector.

In many embodiments, the mechanism further comprises a control cable drive feature and a control cable engaged with the control cable drive feature. The control cable can be routed within the main shaft between the main shaft proximal and distal ends. The mechanism can further comprise an end effector coupled with the control cable. A motion of the control cable can actuate the end effector.

In another aspect, a robotic assembly including an offset drive shaft mounted within a rotating main shaft is provided. The robotic assembly includes a base; a main shaft mounted to rotate relative to the base; a drive shaft mounted inside the main shaft; an actuation assembly coupled with the main shaft and the drive shaft; and an end effector coupled with the main shaft. The main shaft includes a proximal end, a distal end, and a main shaft rotational axis defined therebetween. The drive shaft is offset from the main shaft rotational axis. The actuation assembly is operable to independently rotate the main shaft relative to the base, and rotate the drive shaft relative to the main shaft. The end effector includes a shaft driven mechanism coupled with the drive shaft.

In many embodiments, the robotic assembly further comprises a second drive shaft mounted inside the main shaft and offset from the main shaft rotational axis. The actuation assembly can be further operable to independently rotate the second drive shaft relative to the main shaft. The end effector can further comprise a second shaft driven actuation mechanism operatively coupled with the second drive shaft.

In many embodiments, the robotic assembly further comprises a control cable coupled with the end effector. The control cable can be routed within the main shaft between the main shaft proximal and distal ends. A motion of the control cable can actuate the end effector.

In another aspect, a robotic system including an offset drive shaft mounted within a rotating main shaft is provided. The robotic system includes a base; a main shaft mounted to rotate relative to the base; a first drive shaft mounted inside the main shaft; a second drive shaft mounted inside the main shaft; an actuation assembly coupled with the main shaft, the first drive shaft, and the second drive shaft; a controller; and an end effector coupled with the main shaft so that the end effector is rotated by a rotation of the main shaft. The main shaft includes a proximal end, a distal end, and a main shaft rotational axis defined therebetween. The first drive shaft and the second drive shaft are offset from the main shaft rotational axis. The controller includes an input and an output. The input is coupled with an input device to receive at least one input signal from the input device. The output is coupled with the actuation assembly to output at least one control signal to the actuation assembly. The controller includes a processor and a tangible medium containing instructions that when executed cause the processor to generate the at least one control signal in response to the at least one input signal so that the input device can be used by a user to independently rotate the main shaft relative to the base, rotate the first drive shaft relative to the main shaft, and rotate the second drive shaft relative to the main shaft. The end effector includes a first shaft driven mechanism coupled with the first drive shaft and a second shaft driven actuation mechanism coupled with the second drive shaft.

In many embodiments, the actuation assembly comprises additional components. For example, the actuation assembly can include a first motor coupled with the first drive shaft and the controller. The actuation assembly can include a second motor coupled with the second drive shaft and the controller. The actuation assembly can include a main shaft motor coupled with the main shaft and the controller. The actuation assembly can include a first encoder coupled with the first motor and the controller. The first encoder can output a first motor position signal to the controller in response to a position of the first motor. The actuation assembly can include a second encoder coupled with the second motor and the controller. The second encoder can output a second motor position signal to the controller in response to a position of the second motor. The actuation assembly can include a main shaft encoder coupled with the main shaft motor and the controller. The main shaft encoder can output a main shaft position signal to the controller in response to a position of the main shaft motor.

In many embodiments, the robotic system further comprises a control cable coupled with the end effector. The control cable can be routed within the main shaft between the main shaft proximal and distal ends. A motion of the control cable can actuate the end effector.

In another aspect, a robotic tool including an offset drive shaft mounted within a rotating main shaft is provided. The robotic tool is configured for mounting on a manipulator having a tool interface with first, second, and third drive features. The robotic tool includes a proximal tool chassis releasably mountable to the tool interface; a distal end effector having a distal degree of freedom and a shaft driven actuation mechanism; a main shaft having a proximal end adjacent the chassis, a distal end adjacent the end effector, a bore extending therebetween, and a lateral opening distally of the proximal end; and a hybrid cable/shaft drive system operatively coupling the drive features of the tool interface to the end effector when the chassis is mounted to the tool interface. Actuation of the first drive feature rotates the main shaft and the end effector relative to the chassis about a main shaft rotational axis. Cables extending from the chassis distally within the bore of the main shaft couple the distal degree of freedom of the end effector to the second drive feature. The first drive shaft couples the shaft driven actuation mechanism of the end effector to the third drive feature through the lateral opening in the main shaft. The first drive shaft is offset from the main shaft rotational axis.

In another aspect, a method for transmitting torque through an offset drive shaft routed within a rotatable main shaft is provided. The method includes supporting a main shaft to rotate relative to a base so that the main shaft rotates about a main shaft rotational axis, supporting a drive shaft to rotate relative to the main shaft so that the drive shaft rotates about a drive shaft rotational axis that is offset from the main shaft rotational axis, engaging the drive shaft with a drive feature having a drive feature rotational axis that is fixed relative to the base as the main shaft rotates, rotating the main shaft relative to the base, and rotating the drive feature relative to the main shaft so as to rotate the drive shaft relative to the main shaft. In many embodiments, the main shaft rotates relative to the base and the drive shaft rotates relative to the main shaft simultaneously.

In another aspect, a minimally invasive surgical method is provided. The method includes introducing an end effector to an internal surgical site within a patient through a minimally invasive aperture or natural orifice by manipulating a base, rotating the end effector relative to the base, and performing a surgical task with the end effector by rotating a first drive shaft relative to the instrument shaft so that the first drive shaft actuates the end effector. In the method, the end effector is supported relative to the base by an elongated instrument shaft, the end effector is rotated relative to the base by rotating the instrument shaft relative to the base about an instrument shaft rotational axis, and the first drive shaft rotates relative to the instrument shaft about a first drive shaft rotational axis that is offset from the instrument shaft rotational axis. In many embodiments, the method further comprises actuating the end effector by rotating a second drive shaft relative to the instrument shaft, the second drive shaft rotating about a second drive shaft rotational axis that is offset from the instrument shaft rotational axis.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 7 diagrammatically illustrates the integration of components of the robotic assembly of FIG. 6 with a controller, in accordance with many embodiments.

FIG. 8 diagrammatically illustrates a robotic tool and an associated robotic system, in accordance with many embodiments.

FIG. 15A is a perspective view of a main shaft coupling fitting used to couple a rotatable main shaft with a proximal tool chassis, showing openings through which internally mounted offset drive shafts are driven and external gear teeth that are used to rotate the main shaft, in accordance with many embodiments.

FIG. 15B is a perspective view of an internal subassembly that includes two internal offset drive shafts and associated support fittings, in accordance with many embodiments.

FIG. 15C is a perspective view showing the combination of the components of FIGS. 15A and 15B, in accordance with many embodiments.

FIG. 15D is an end view showing the combination of the components of FIGS. 15A and 15B, in accordance with many embodiments.

DETAILED DESCRIPTION

Mechanisms, assemblies, systems, tools, and methods incorporating the use of an offset drive shaft within an independently rotating member are provided. Such mechanisms, assemblies, systems, tools, and methods may be particularly beneficial for use in surgery, for example, in minimally invasive surgery, minimally invasive robotic surgery, as well as other types of surgery. While the various embodiments disclosed herein are primarily described with regard to surgical applications, related mechanisms, assemblies, systems, tools, and methods can be used in a wide variety of applications, both inside and outside a human body, as well as in non-surgical applications.

Minimally Invasive Robotic Surgery

Figure 1:
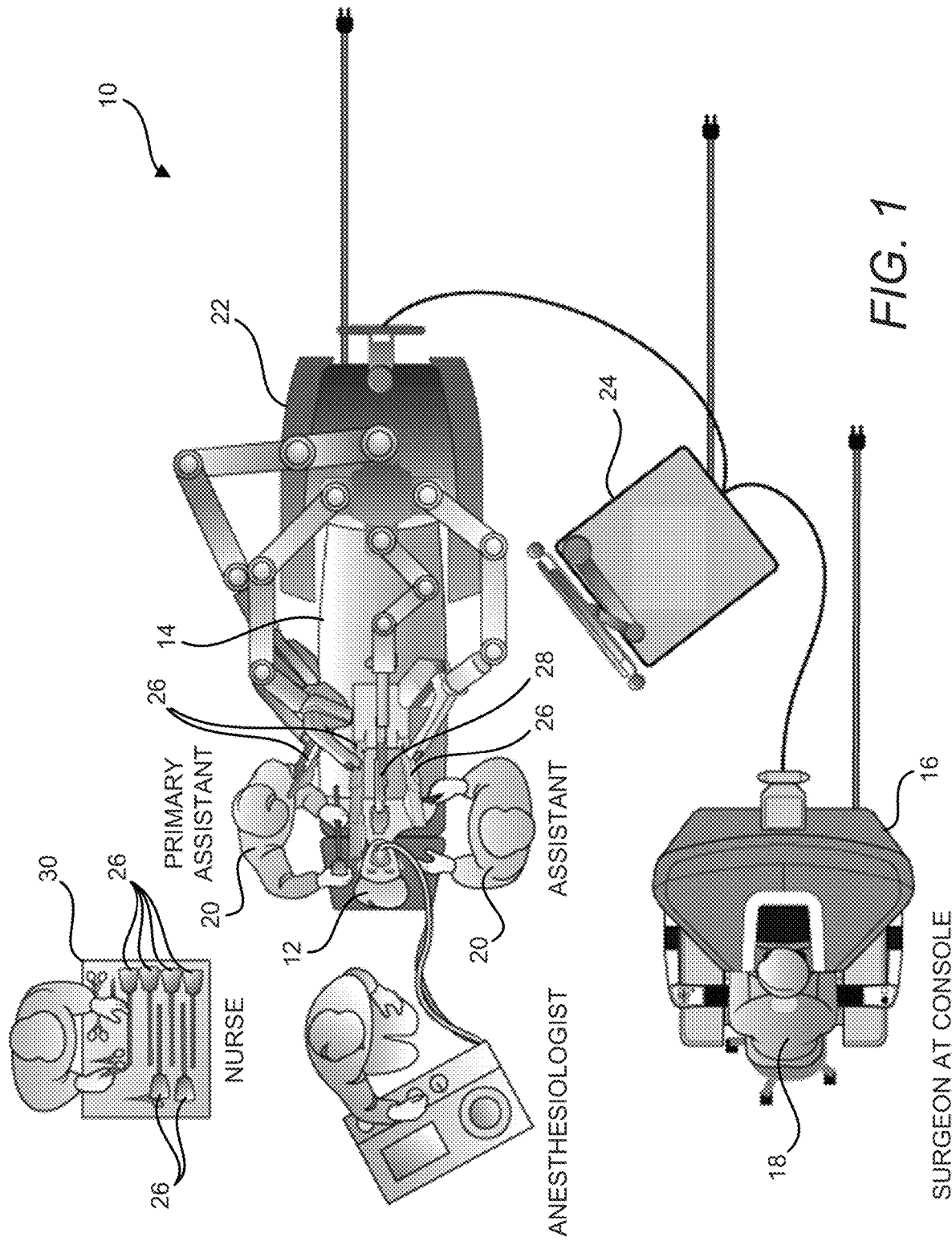
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot), and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
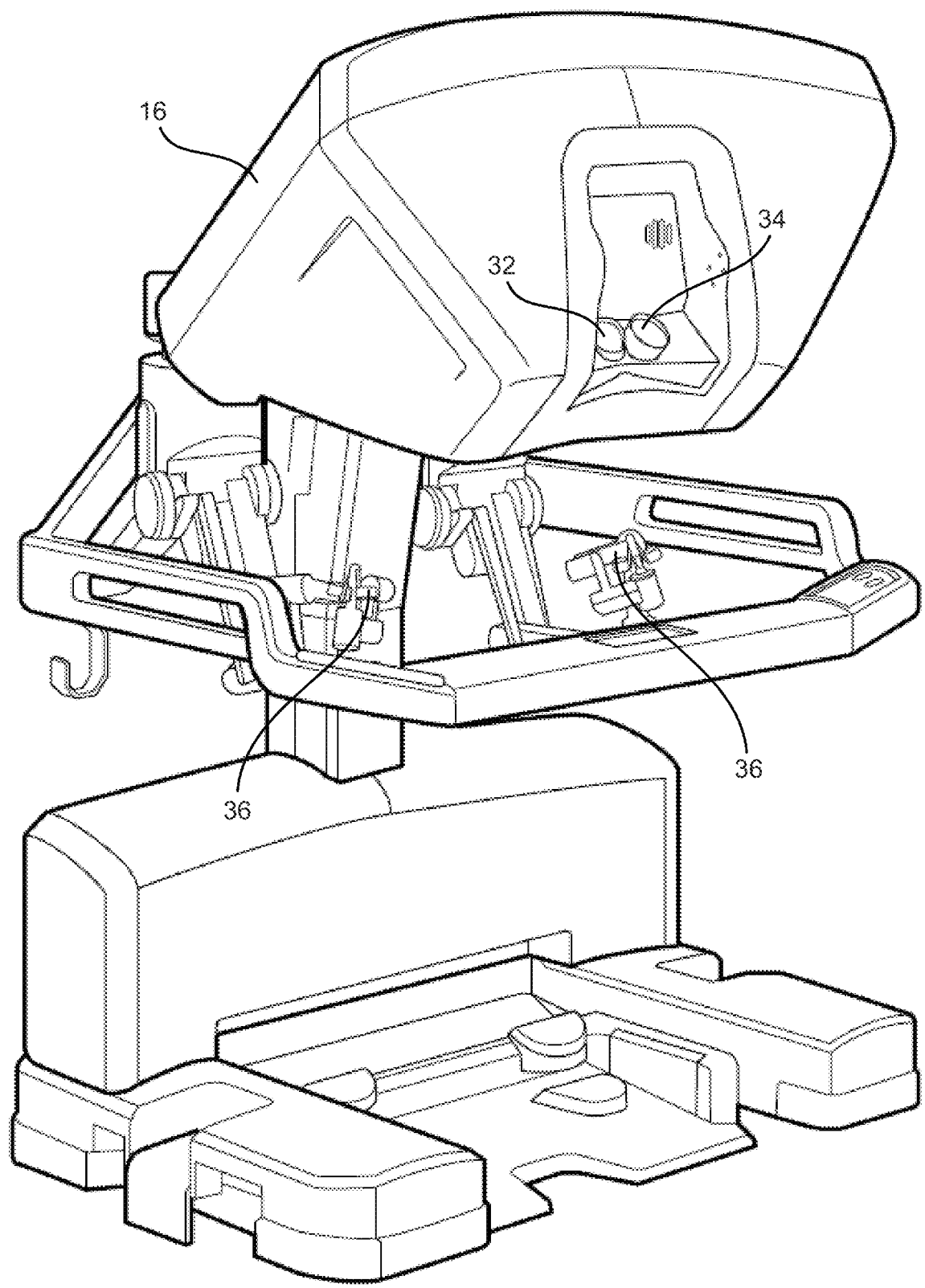
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 will provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
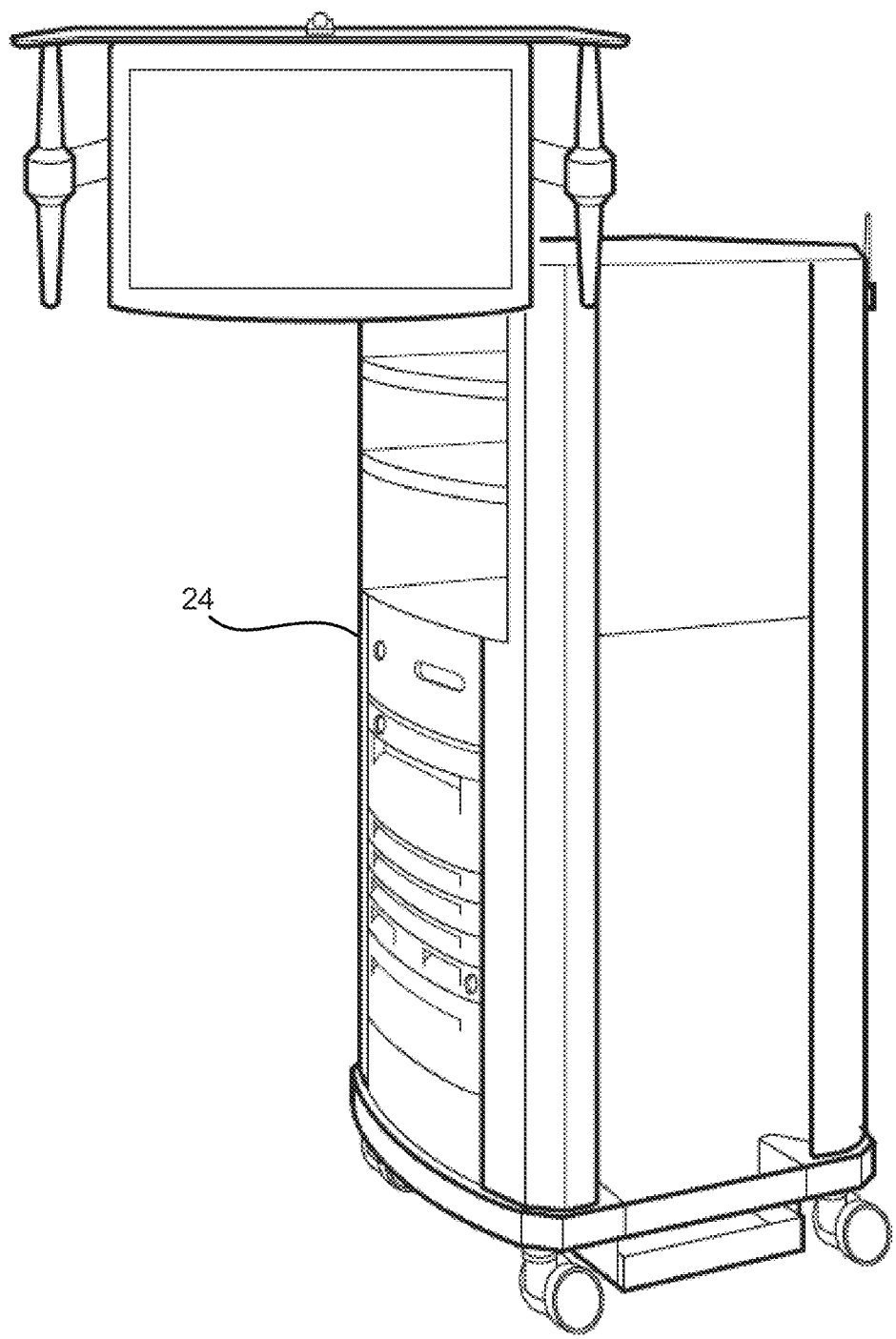
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
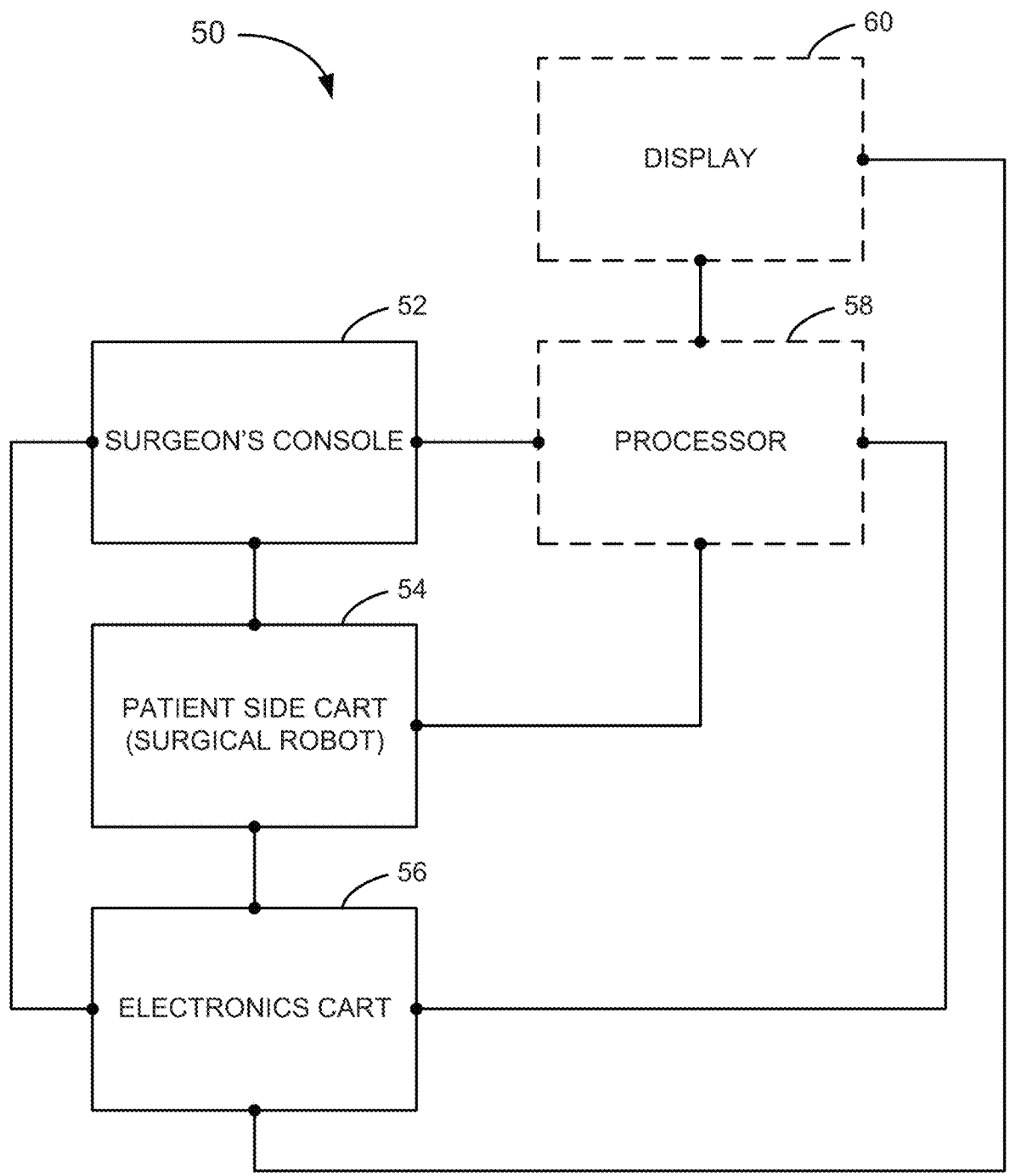
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5B:
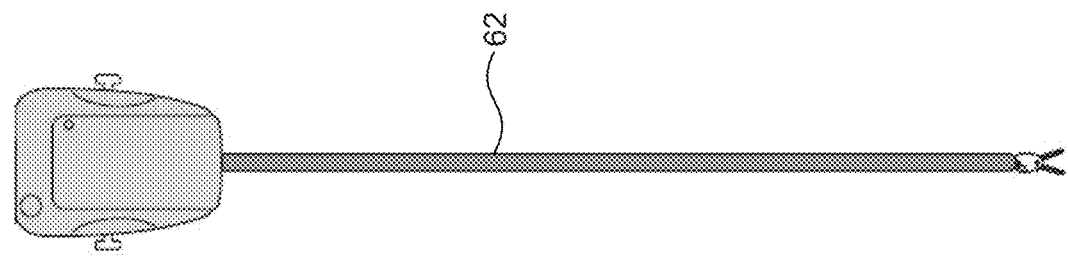
FIG. 5B is a front view of a robotic surgery tool.
Figure 5A:
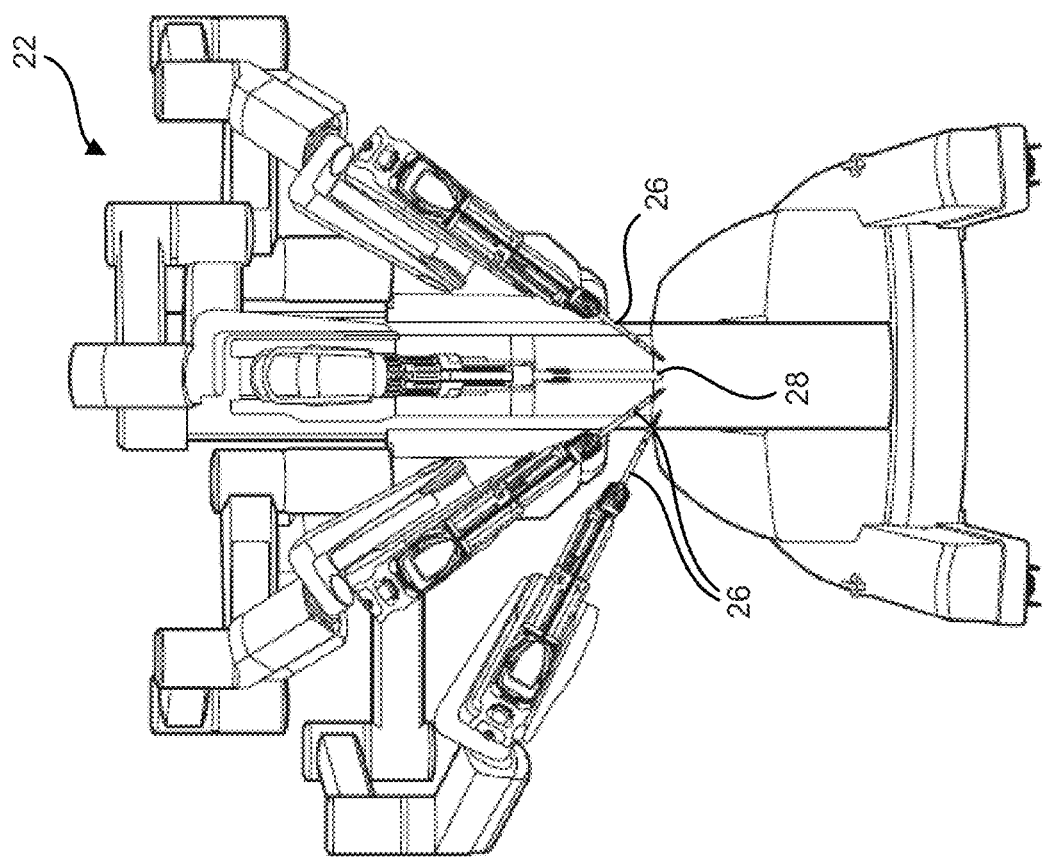
FIG. 5A is a front view of a patient side cart (surgical robot) of a robotic surgery system, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Offset Drive Shaft(s) Within a Rotatable Shaft

Figure 6:
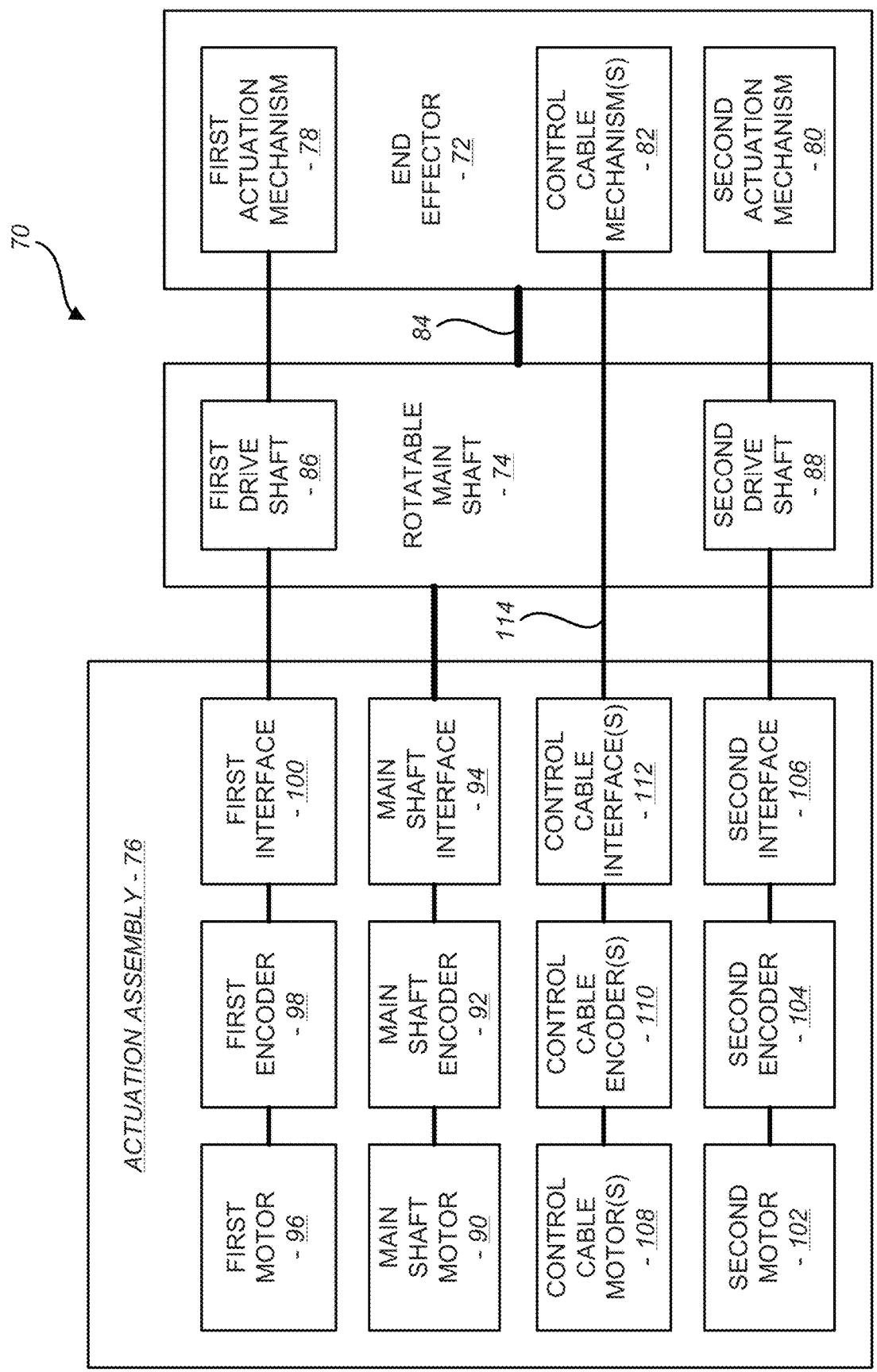
FIG. 6 diagrammatically illustrates a robotic assembly having two offset drive shafts within a rotatable main shaft, in accordance with many embodiments.

FIG. 6 diagrammatically illustrates a robotic assembly 70 having two offset drive shafts within a rotatable main shaft, in accordance with many embodiments. The robotic assembly 70 includes an end effector 72 that is coupled with the distal end of a rotatable main shaft 74, and an actuation assembly 76 coupled with both the main shaft 74 and the end effector 72.

The end effector 72 includes an end effector base, a first actuation mechanism 78, a second actuation mechanism 80, and a control cable mechanism(s) 82. The end effector base is pivotally coupled to the rotatable main shaft 74. The first actuation mechanism 78 and the second actuation mechanism 80 are shaft driven and can be used to actuate and/or articulate a variety of end effector features and/or devices, for example, a clamping feature, a movable cutting feature, a cutting and stapling device, or another suitable end effector feature and/or device that can be actuated and/or articulated with a shaft driven mechanism. The control cable mechanism(s) 82 can also be used to actuate and/or articulate a variety of end effector features and/or devices, particularly those where a fast response is desired, for example, a grasping feature, a main shaft to end effector base wrist that is used to articulate the end effector base relative to the main shaft, or another suitable feature and/or device that can be actuated and/or articulated via one or more control cables.

The end effector base is coupled with the rotatable main shaft 74 so that a rotation of the main shaft 74 about a main shaft rotation axis produces a corresponding rotation of the end effector base. As discussed above, the ability to independently rotate the main shaft 74 provides increased end effector maneuverability relative to a non rotating main shaft, which may be beneficial during certain surgical procedures, for example, during certain minimally invasive surgical procedures. The end effector base can also be coupled with the rotatable main shaft 74 with a suitable wrist mechanism 84 that provides additional end effector maneuverability.

Two drive shafts are used to drive the end effector shaft driven actuation mechanisms. A first drive shaft 86 is mounted for rotation about a first drive shaft rotational axis that is offset from the main shaft rotation axis. The first drive shaft 86 is operatively coupled with the first actuation mechanism 78. Likewise, a second drive shaft 88 is mounted for rotation about a second drive shaft rotational axis that is offset from the main shaft rotation axis. The second drive shaft 88 is operatively coupled with the second actuation mechanism 80.

The actuation assembly 76 is coupled with the rotatable main shaft 74, the first drive shaft 86, the second drive shaft 88, and the control cable mechanism(s) 82. The rotatable main shaft 74 is mounted for rotation relative to a base of the actuation assembly 76. The actuation assembly 76 is operable to produce rotation of the rotatable main shaft 74 relative to the base. The actuation assembly 76 is also operable to generate any combination of rotation of the rotatable main shaft 74 relative to the base, rotation of the first drive shaft 86 relative to the rotatable main shaft 74, and rotation of the second drive shaft 88 relative to the rotatable main shaft 74. As such, the first actuation mechanism 78 and/or the second actuation mechanism 80 can be actuated independently and/or simultaneously with rotation of the rotatable main shaft 74.

The actuation assembly 76 is configured to provide the above described functionality in which the first drive shaft 86 and the second drive shaft 88 can be independently rotated relative to the rotatable main shaft 74, even during rotation of the rotatable main shaft 74 relative to the base. The actuation assembly 76 includes a main shaft motor 90 coupled with a main shaft encoder 92 and a main shaft interface 94, a first motor 96 coupled with a first encoder 98 and a first interface 100, a second motor 102 coupled with a second encoder 104 and a second interface 106, and a control cable motor(s) 108 coupled with a control cable encoder(s) 110 and a control cable interface(s) 112. The main shaft interface 94 is coupled with the rotatable main shaft 74 so as to transfer rotational motion from the main shaft motor 90 to the rotatable main shaft 74. The main shaft motor 90 can be fixedly coupled with the base so that the transferred rotational motion results in rotation of the rotatable main shaft 74 relative to the base. The main shaft encoder 92 measures the orientation of the main shaft motor 90, the main shaft interface 94, and/or the rotatable main shaft 74 and can be coupled with a controller (not shown in FIG. 6) so as to provide the controller with the measured orientation. The first interface 100 is coupled with the first drive shaft 86 so as to be operable to transfer rotational motion from the first motor 96 to the first drive shaft 86 during any orientation and/or rotational motion of the rotatable main shaft 74. The first encoder 98 measures the orientation of the first motor 96, the first interface 100, and/or the first drive shaft 86 and can be coupled with the controller so as to provide the controller with the measured orientation. The second interface 106 is coupled with the second drive shaft 88 so as to be operable to transfer rotational motion from the second motor 102 to the second drive shaft 88 during any orientation and/or rotational motion of the rotatable main shaft 74. The second encoder 104 measures the orientation of the second motor 102, the second interface 106, and/or the second drive shaft 88 and can be coupled with the controller so as to provide the controller with the measured orientation. The control cable interface(s) 112 is coupled with control cable(s) 114 that are operatively coupled with the control cable mechanism(s) 82. The control cable(s) 114 can be routed so as to tolerate a range of rotational orientations of the rotatable main shaft 74, for example, by being routed in the vicinity of the main shaft rotational axis to minimize changes in control cable length due to rotation of the rotatable main shaft 74, and by being configured to tolerate any twisting of control cable(s) and/or twisting between control cables that may result for some rotational orientations of the main shaft 74 (e.g., by having a construction that tolerates cable-to-cable rubbing). The control cable encoder(s) 110 measures the orientation of the control cable motor(s) 108 and/or the control cable interface(s) 112 and can be coupled with the controller so as to provide the controller with the measured orientation(s).

FIG. 7 is a simplified block diagram illustrating the integration of components of the robotic assembly 70 with a controller 116, in accordance with many embodiments. The controller 116 includes at least one processor 118, which communicates with a number of peripheral devices via a bus subsystem 120. These peripheral devices typically include a storage subsystem 122.

The storage subsystem 122 maintains the basic programming and data constructs that provide the functionality of the controller 116. Software modules for implementing the robotic assembly functionality discussed above are typically stored in the storage subsystem 122. The storage subsystem 122 typically includes a memory subsystem 124 and a file storage subsystem 126.

The memory subsystem 124 typically includes a number of memories including a main random access memory (RAM) 128 for storage of instructions and data during program execution and a read only memory (ROM) 130, in which fixed instructions are stored.

The file storage subsystem 126 provides persistent (non-volatile) storage for program and data files, and can include a hard drive, a disk drive, or other non-volatile memory such as a flash memory. An input device, for example a disk drive, can be used to input the software modules discussed above. Alternatively, other known structures may alternatively be used to input the software modules, for example, a USB port.

In this context, the term "bus subsystem" is used generically so as to include any mechanism for letting the various components and subsystems communicate with each other as intended. The bus subsystem 120 is shown schematically as a single bus, but a typical system has a number of buses such as a local bus and one or more expansion buses (e.g., ADB, SCSI, ISA, EISA, MCA, NuBus, or PCI), as well as serial and parallel ports.

The controller 116 controls components of the robotic assembly 70 in response to assorted received signals, including signals from the input control device(s) 36 (shown in FIG. 2), as well as from the main shaft encoder 92, the first encoder 98, the second encoder 104, and the control cable encoder(s) 110. The components controlled include the main shaft motor 90, the first motor 96, the second motor 102, and the control cable motor(s) 108. Additional components (not shown), such as digital/analog converters can be used to interface components with the controller 116.

FIG. 8 is a simplified block diagram illustrating the integration of a robotic surgery tool 132 within a robotic surgery system, in accordance with many embodiments. The tool 132 includes a proximal tool chassis 134 configured to be releasably mountable on a manipulator 136 having a tool interface configured to interface with the proximal tool chassis 134. The tool 132 further includes an elongate main shaft 74 that is mounted to rotate relative to the proximal tool chassis 134 when rotated by a main shaft motor, as discussed above. An end effector 140 is coupled with a distal end of the main shaft 74 so as to rotate along with the main shaft. A main control system 142 is operatively coupled with the manipulator 136. An auxiliary control system 144 can also be operatively coupled with the manipulator 136. The combination of the main control system 142 and the auxiliary control system 144 can be used to control all possible articulations of the tool 132 via the manipulator 136. For example, the auxiliary control system 144 can control the drive motors for first drive shaft rotation and second drive shaft rotation. The main control system 142 can control a drive motor for main shaft rotation and one or more control cable drive motors. Such an auxiliary controller can be used to supplement existing robotic surgery system configurations so as to allow the use of the presently disclosed robotic tools having one or more offset drive shafts routed within an independently rotating main shaft.

Figure 9:
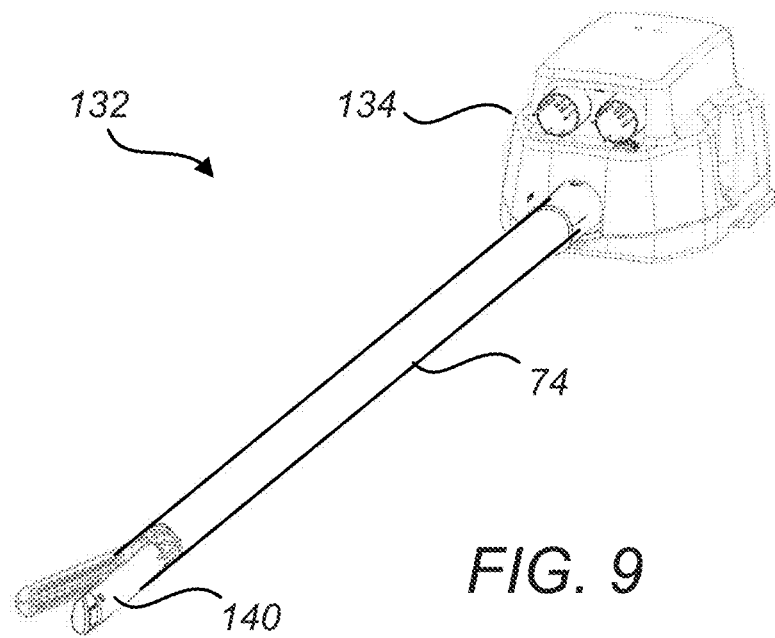
FIG. 9 is a perspective view of a robotic tool that is releasably mountable to a robotic tool manipulator, in accordance with many embodiments.

FIG. 9 is a perspective view of a robotic surgery tool 132, in accordance with many embodiments. As discussed above, the tool 132 includes a proximal tool chassis 134 configured to be releasably mountable on a tool manipulator 136. The rotatable main shaft 74 couples the end effector 140 with the proximal tool chassis 134.

Figure 10:
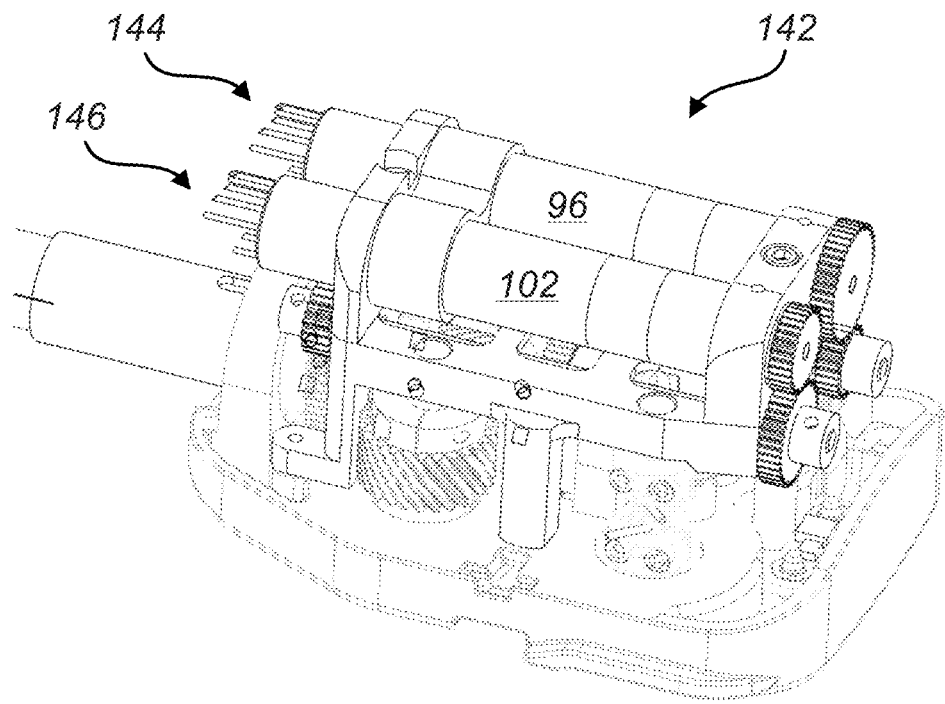
FIG. 10 is a perspective view of the proximal end of a robotic tool of FIG. 9, showing an actuation assembly, in accordance with many embodiments.

FIG. 10 is a perspective view of the proximal tool chassis 134 of FIG. 9 (without the cover), showing an actuation assembly 142, in accordance with many embodiments. The actuation assembly 142 includes a first motor 96 for actuating a first offset drive shaft and a second motor 102 for actuating a second offset drive shaft. The various encoders discussed above (e.g., the main shaft encoder 92, the first encoder 98, the second encoder 104, and the control cable encoder(s) 110) can be integrated within the actuation assembly 142. The first motor 96 is coupled with a set of electrical connection pins 144 configured to couple with a mating electrical connector that is coupled with a controller for selectively driving the first motor 96. Likewise, the second motor 102 is coupled with a set of electrical connection pins 146 configured to couple with a mating electrical connector that is coupled with the controller for selectively driving the second motor 102.

Figure 11:
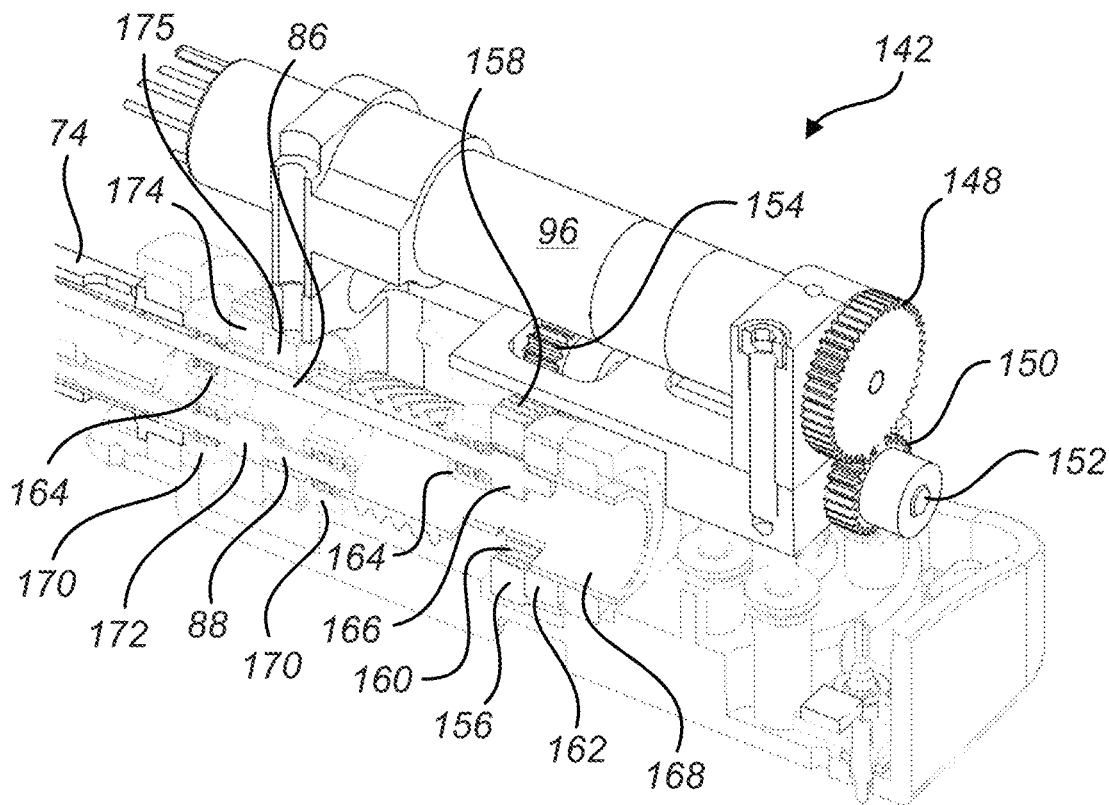
FIG. 11 is a perspective view of a cross section of the actuation assembly of FIG. 10, illustrating components used to actuate a first offset internal drive shaft, in accordance with many embodiments.

FIG. 11 is a perspective view of a cross section of the actuation assembly 142 of FIG. 10, illustrating components used to actuate a first offset internal drive shaft, in accordance with many embodiments. The first motor 96 is rotationally coupled with a first motor gear 148. The first motor gear 148 engages and drives a first coupling shaft proximal gear 150, which drives a first coupling shaft 152. The coupling shaft 152 in turn rotates a first coupling shaft distal gear 154. The first coupling shaft distal gear 154 engages a first annular gear 156, which includes both external gear teeth 158 that engage the first coupling shaft distal gear 154 and internal ring gear teeth 160. The first annular gear 156 is mounted to rotate about the centerline of the rotatable main shaft 74 via a first annular gear bearing 162. The first drive shaft 86 is mounted to rotate about a first drive shaft rotation axis that is offset from the rotatable main shaft rotation axis. The first drive shaft 86 is mounted to the main shaft via two first drive shaft support bearings 164. The first drive shaft 86 is coupled with a first drive shaft gear 166, which includes external gear teeth that protrude from an opening in a main shaft coupling fitting 168 so as to engage the internal gear teeth 160 of the first annular gear 156. In operation, rotation of the first motor 96 rotates the first motor gear 148, which rotates the first coupling shaft proximal gear 150, which rotates the coupling shaft 152, which rotates the first coupling shaft distal gear 154, which rotates the first annular gear 156, which rotates the first drive shaft gear 166, which rotates the first drive shaft 86 relative to the main shaft 74.

In many embodiments, the actuation assembly 142 is designed to accommodate a range of axial motion of the first drive shaft 86, for example, by designing the first annular gear 156 and the opening in the main shaft coupling fitting 168 for a range of axial motion of the first drive shaft 86 (e.g., by increasing the dimension of the opening and the annular gear 156 in the direction of the axial motion of the first drive shaft 86 over a size sufficient to accommodate the protruding gear teeth of the first drive shaft gear 166 thereby allowing the first drive shaft gear 166 to slide axially relative to the internal ring gear teeth of the first annular gear 156). Such axial motion of the first drive shaft 86 may occur during articulation of an end effector base relative to the main shaft where the end effector base rotates about a wrist axis that is offset from the centerline of the first drive shaft 86.

FIG. 11 also illustrates actuation components used to actuate the second offset internal drive shaft 88, in accordance with many embodiments. The second drive shaft 88 is mounted to rotate about a second drive shaft rotation axis that is offset from the rotatable main shaft rotation axis. The second drive shaft 88 is mounted to the main shaft via second drive shaft support bearings 170. The second drive shaft 88 is coupled with a second drive shaft gear 172, which includes external gear teeth that protrude from an opening in a main shaft coupling fitting 168 so as to engage internal ring gear teeth of a second annular gear 174. The second annular gear 174 is mounted to rotate about the centerline of the rotatable main shaft 74 via a second annular gear bearing 175. As discussed above with regard to the first drive shaft, the actuation assembly 142 can also be designed to accommodate a range of axial motion of the second drive shaft 88, for example, by designing the second annular gear 174 and the opening in the main shaft coupling fitting 168 for a range of axial motion of the second drive shaft 88.

Figure 12:
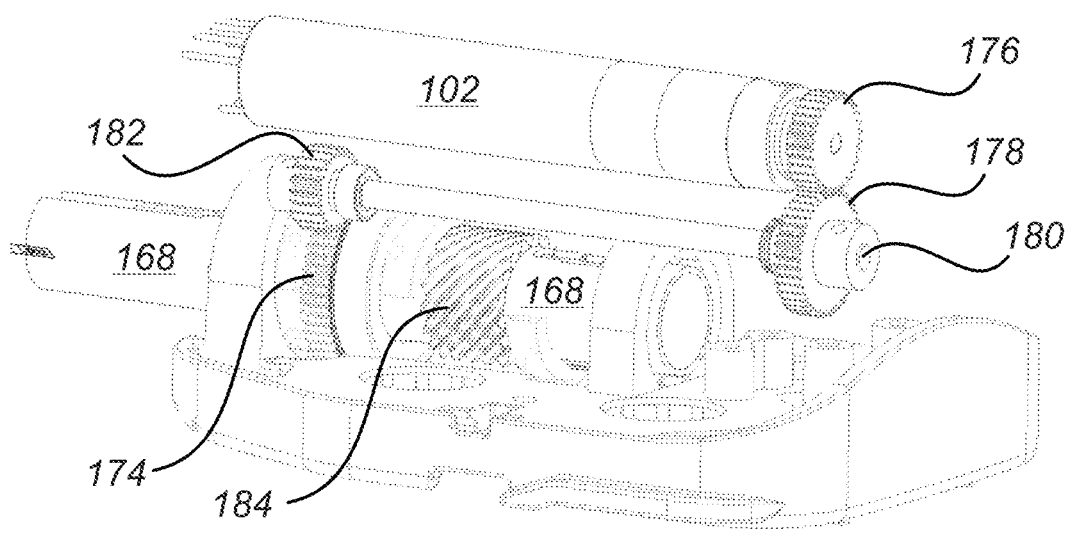
FIG. 12 is a perspective view illustrating components of the actuation assembly of FIG. 10 that are used to actuate a second offset internal drive shaft, in accordance with many embodiments.

FIG. 12 is a perspective view illustrating components of the actuation assembly 142 of FIG. 10 that are used to actuate a second offset internal drive shaft, in accordance with many embodiments. The second motor 102 is rotationally coupled with a second motor gear 176. The second motor gear 176 engages and drives a second coupling shaft proximal gear 178, which drives a second coupling shaft 180. The second coupling shaft 180 in turn rotates a second coupling shaft distal gear 182. The second coupling shaft distal gear 182 engages the second annular gear 174, which includes both external gear teeth that engage the second coupling shaft distal gear 182 and internal ring gear teeth. The second annular gear 174 is mounted to rotate about the centerline of the rotatable main shaft via a second annular gear bearing. In operation, rotation of the second motor 102 rotates the second motor gear 176, which rotates the second coupling shaft proximal gear 178, which rotates the second coupling shaft 180, which rotates the second coupling shaft distal gear 182, which rotates the second annular gear 174, which rotates the second drive shaft gear 172, which rotates the second drive shaft 88 relative to the rotatable main shaft 74.

In many embodiments, the main shaft coupling fitting 168 includes external gear teeth 184 engaged with a main shaft interface 94 (not shown) that is driven by the main shaft motor 90 (not shown.) The main shaft interface 94 and the main shaft motor 90 can be located on a tool manipulator 136 (shown in FIG. 8) so as to be coupled with the main shaft coupling fitting 168 when the proximal tool chassis 134 is mounted on a tool manipulator 136.

Figure 13:
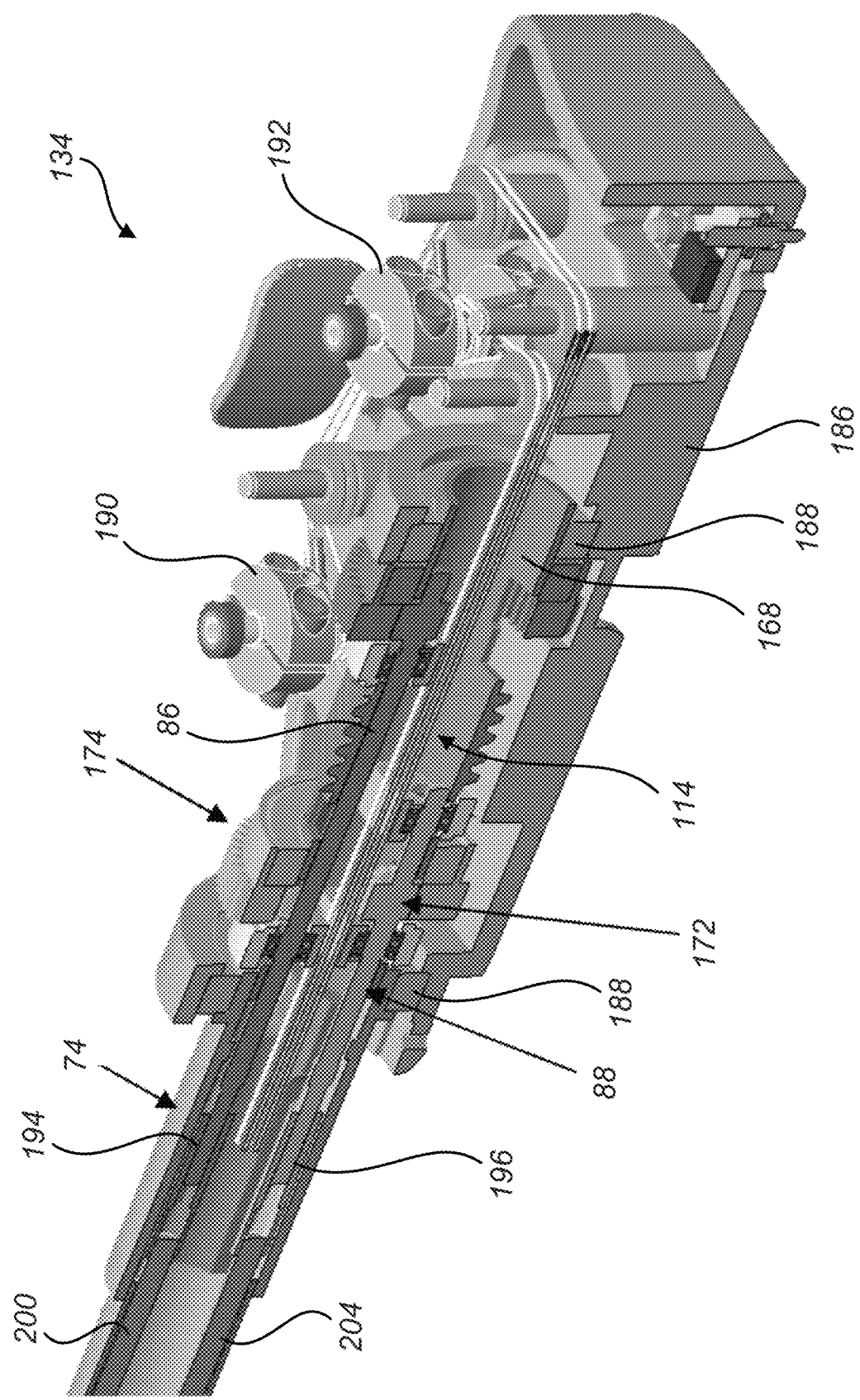
FIG. 13 is a perspective view of a cross section of the actuation assembly of FIG. 10, illustrating various components and the routing of end effector control cables, in accordance with many embodiments.

FIG. 13 is a perspective view of a cross section of components of the actuation assembly of FIG. 10, illustrating various components and the routing of end effector control cables, in accordance with many embodiments. The proximal tool chassis 134 includes a base 186 that provides a mounting base for various components. The main shaft coupling fitting 168 is mounted to rotate relative to the base 186 via two bearings 188. The main shaft coupling fitting 168 supports the rotatable main shaft 74. The main shaft 74 has an axial bore through which the first drive shaft 86, the second drive shaft 88, and two pairs of control cables 114 are routed. The first drive shaft 86 and the second drive shaft 88 are offset from the centerline of the main shaft coupling fitting 168 and the rotatable main shaft 74, which allows the control cables 114 to be routed along the centerline of the main shaft. In many embodiments, rotation of the main shaft relative to the base produces twisting of control cables 114 due to the corresponding rotation of the end effector base relative to the proximal chassis base 186. Routing the control cables 114 along the centerline of the main shaft may help to reduce detrimental impacts to the operation of the control cables that may occur in connection with such twisting, for example, by reducing cable to cable frictional forces and/or by reducing associated control cable stretching.

In many embodiments, a pair of control cables is actuated by a common actuation mechanism, for example, by a capstan around which the pair of control cables is wrapped. Such a common actuation mechanism can be used to retract one control cable of a pair of control cables while the other control cable of the pair is let out by a corresponding amount. FIG. 13 illustrates a first capstan 190 for actuating a first control cable pair and a second capstan 192 for actuating a second control cable pair.

In many embodiments, the first drive shaft 86 is rotationally coupled with a first drive shaft extension 200 via a first splined coupling 194 that couples a distal end of the first drive shaft 86 with a proximal end of the first drive shaft extension 200. The first splined coupling 194 can be used to enable the use of a conveniently sized first drive shaft 86, for example, so that the first drive shaft 86 can be produced without undue expense, and so as to be more easily assembled into the overall assembly. The first splined coupling 194 can also provide for the accommodation of a range of axial motion of the first drive shaft extension 200, which, as discussed above, may result during the articulation of the end effector base relative to the main shaft due to the first drive shaft extension 200 being offset from the main shaft centerline. Likewise, a second splined coupling 196 can be used in connection with the second offset drive shaft 88, and may provide similar benefits.

Figure 14:
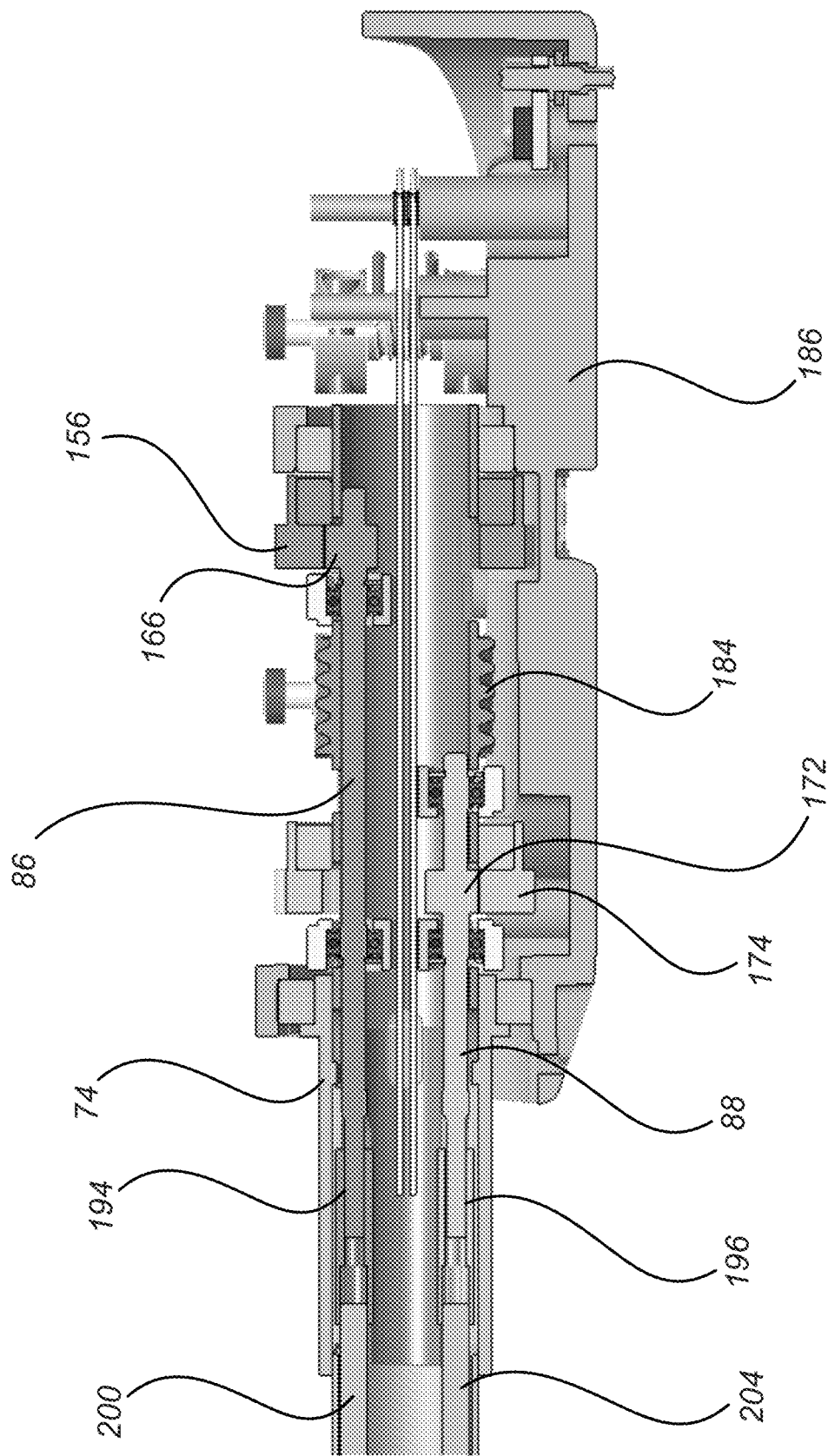
FIG. 14 is a cross-sectional view of the actuation assembly of FIG. 10, illustrating various components and the routing of end effector control cables, in accordance with many embodiments.

FIG. 14 is a cross-sectional view of components of the actuation assembly of FIG. 10, further illustrating various components and the routing of end effector control cables, in accordance with many embodiments. The internal ring gear teeth of the first annular gear 156 interact with the first drive shaft gear 166 so that rotation of the first annular gear 156 relative to the main shaft coupling fitting produces a corresponding rotation of the first drive shaft 86 relative to the main shaft coupling fitting. The internal ring gear teeth of the second annular gear 174 interact with the second drive shaft gear 172 so that rotation of the second annular gear 174 relative to the main shaft coupling fitting produces a corresponding rotation of the second drive shaft 88 relative to the main shaft coupling fitting.

FIG. 15A is a perspective view of the main shaft coupling fitting 168, in accordance with many embodiments. The main shaft coupling fitting 168 includes a number of openings, slots, fastener holes, as well as external gear teeth. A first opening 206 accommodates the protruding gear teeth of the first drive shaft gear 166. A second opening 208 accommodates the protruding gear teeth of the second drive shaft gear 172. A third opening 210 accommodates a protruding feature of a drive shaft bearing support fitting used to support the proximal end of the second drive shaft. A number of fastener holes 212 are provided that accommodate drive shaft support bearing mounting fasteners. In many embodiments, the main shaft coupling fitting 168 includes symmetrical features so as to allow for a reversible installation of the first and second drive shafts. The external gear teeth 184 are used to rotate the main shaft coupling fitting 168 relative to the base of the proximal tool chassis. Two slots 214 accommodate the first splined coupling 194 and the second splined coupling 196.

FIG. 15B is a perspective view of an internal subassembly that includes the two internal offset drive shafts and associated support bearing mounting components, in accordance with many embodiments. The first drive shaft proximal portion 198 and the second drive shaft proximal portion 202 are received within bearings that are supported by four internal support fittings 216. The four internal support fittings 216 are held in position within the main shaft coupling fitting 168 via a corresponding four external support fittings 218, which are coupled with the internal support fittings 216 via two fasteners 220 per fitting pair.

FIGS. 15C and 15D are views showing the combination of the components of FIGS. 15A and 15B, in accordance with many embodiments. FIG. 15C is a perspective view of the combination and FIG. 15D shows an end view, which shows the fasteners 220, the external gear teeth 184, an external support fitting 218, the first drive shaft gear 166, the second drive shaft gear 172, two internal support fittings 216, and a retainer ring 222 used to secure the second drive shaft proximal end relative to an internal support fitting 216. A central space 224 located between adjacent internal support fittings 216 accommodates the routing of the control cables (not shown).

Figure 16:
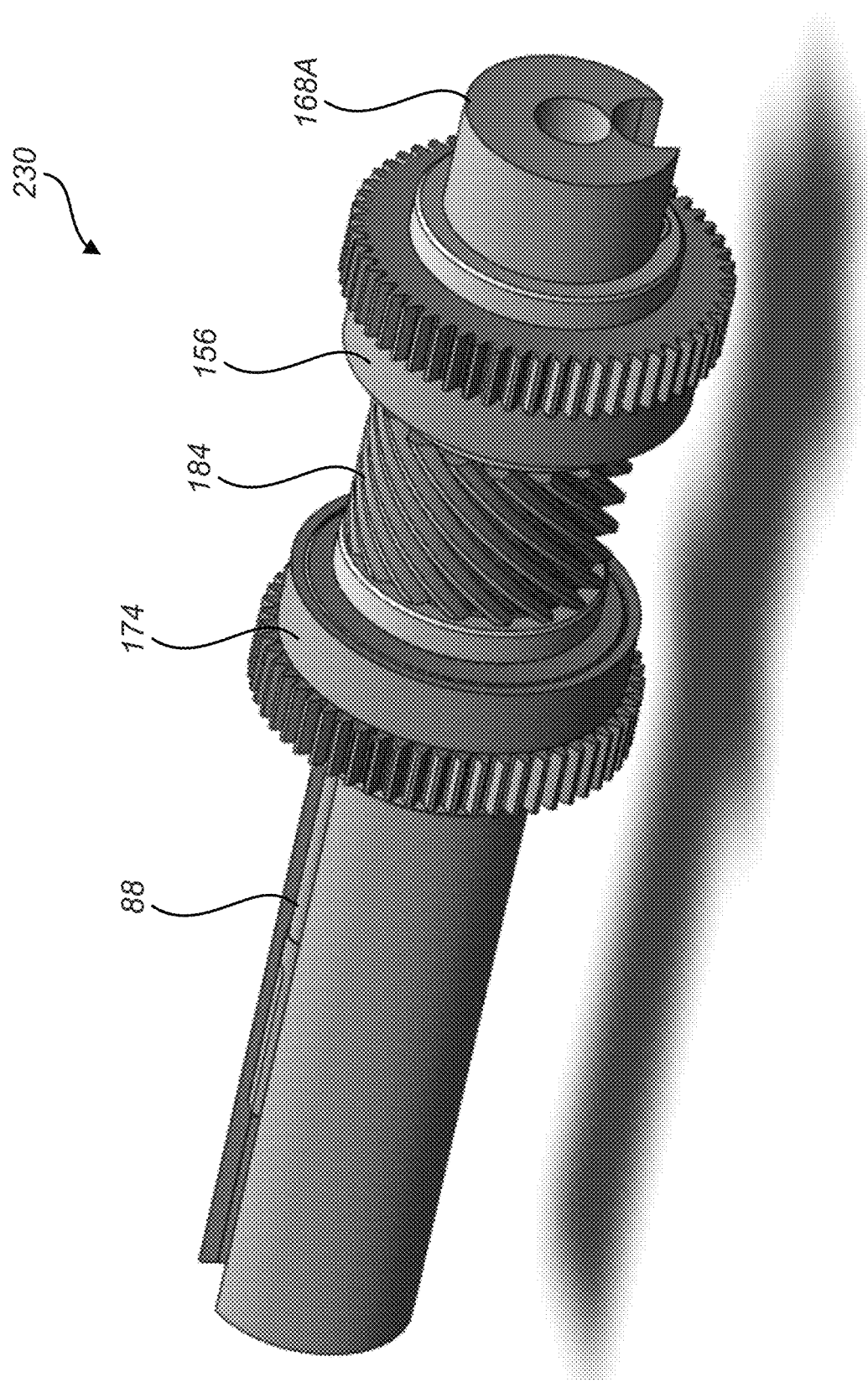
FIG. 16 is a perspective view of an actuation assembly having a reduced part count configuration, in accordance with many embodiments.

Alternative approaches can be used to support an offset internal drive shaft. For example, FIG. 16 is a perspective view of an actuation assembly 230 having a reduced part count configuration. The actuation assembly 230 provides for the independent actuation of the above described two offset drive shaft 86, 88, but eliminates some of the above described components used to support the two offset drive shafts 86, 88. The actuation assembly 230 does include some of the above describe components, for example, the first drive shaft 86 (hidden from view), the second drive shaft 88, the first annular gear 156, and the second annular gear 174. The actuation assembly 230 includes a main shaft coupling fitting 168A that is configured with integrated support for the drive shaft support bearings. Similar to the above described main shaft coupling fitting 168, the main shaft coupling fitting 168A includes external gear teeth 184 for engagement with the above described main shaft interface 94 (not shown).

Figure 17:
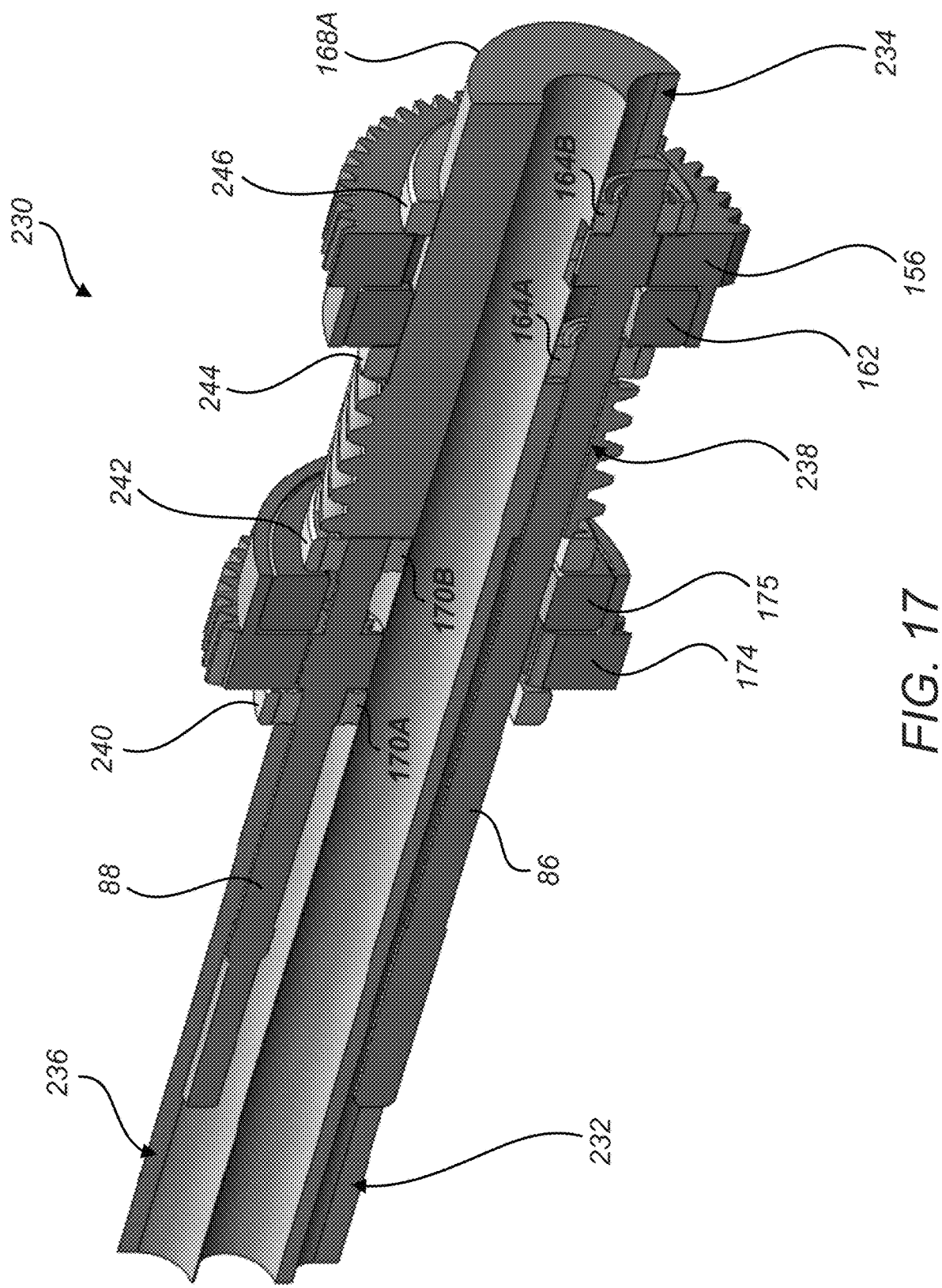
FIG. 17 is a perspective cross-sectional view of the actuation assembly of FIG. 16.

FIG. 17 is a perspective cross-sectional view of the actuation assembly 230, illustrating details of the integration of the support for the drive shaft bearings into the main shaft coupling fitting 168A. The main shaft coupling fitting 168A is configured with externally accessible recesses 232, 234, 236 that interface with first drive shaft support bearings 164A, 164B and second drive shaft support bearings 170A, 170B. Retainer rings 244, 246 are used to retain the support bearings 164A, 164B within the recess 234. Retainer rings 240, 242 are used to retain the support bearings 170A, 170B within the recess 236. The distally disposed recess 232 is shaped to accommodate the distal end of the first drive shaft 86. The proximally disposed recess 234 is shaped to support the proximally disposed support bearings 164A, 164B and to accommodate the proximal end of the first drive shaft 86. The main shaft coupling fitting 168A includes a bore 238 configured to slidingly receive and accommodate the first drive shaft 86. The distally disposed recess 236 is shaped to support the support bearings 170A, 170B and to accommodate the second drive shaft 88.

The first drive shaft 86 can be assembled into the actuation assembly 230 using the following assembly sequence. First, the support bearing 164A is placed in its installed position. The retainer ring 244 is then moved from the proximal end of the main shaft coupling fitting 168A into its installed position. A subassembly comprising the first annular gear 156 and the first annular gear bearing 162 is then moved from the proximal end of the main shaft coupling fitting 168A into its installed position. The first drive shaft 86 is then installed by threading the distal end of the first drive shaft 86 through the support bearing 164A, and through the bore 238. The support bearing 164B is then slid along the recess 234 into its installed position. Finally, the retainer ring 246 is then moved from the proximal end of the main shaft coupling fitting 168A into its installed position. A similar sequence can be used for the installation of the second drive shaft 88 into the actuation assembly 230.

Figure 18A:
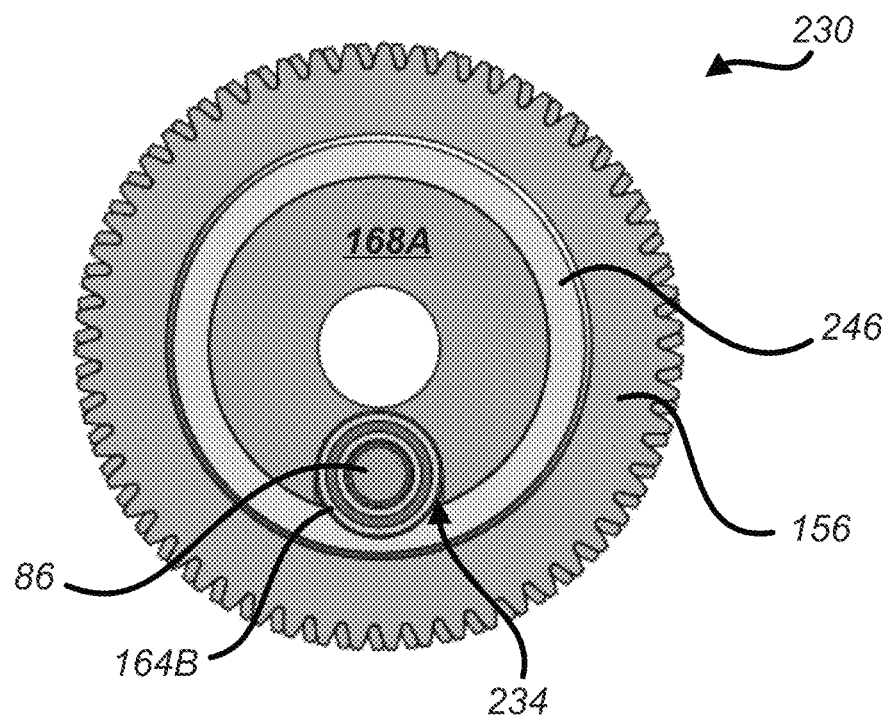
FIGS. 18A and 18B are proximal and distal end views, respectively, of the actuation assembly of FIG. 16.
Figure 18B:
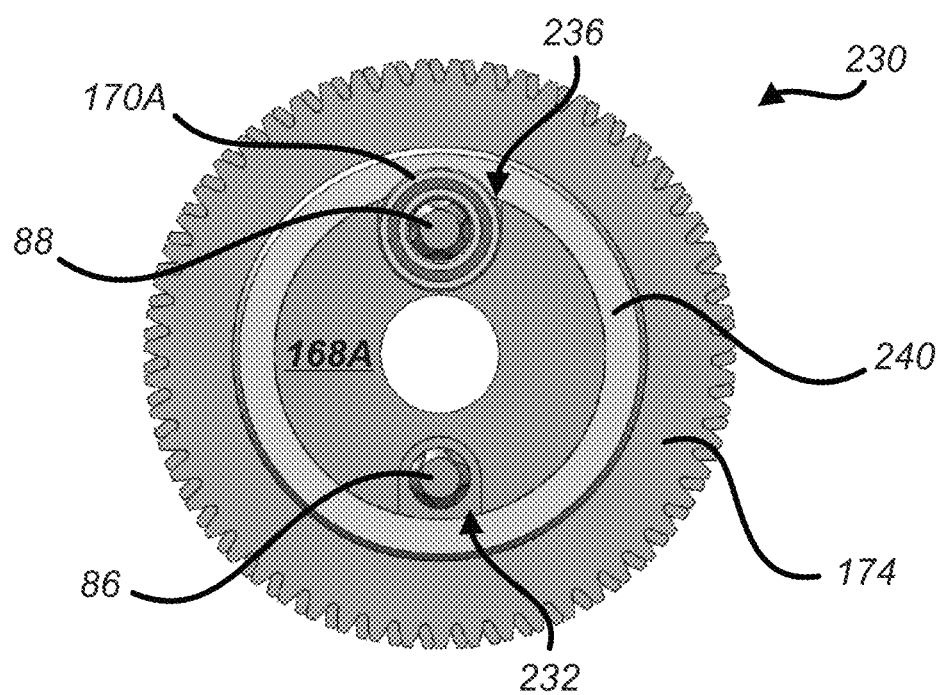

FIGS. 18A and 18B are proximal and distal end views, respectively, of the actuation assembly 230. FIG. 18A shows the proximally located support bearing 164B relative to the proximal recess 234 and the first drive shaft 86. The retainer rings 240, 242, 244, 246 are locally shaped to accommodate the support bearings 170A, 170B, 164A, 164B, respectively. FIG. 18B shows the distal ends of the first drive shaft 86 and the second drive shaft 88, the associated recesses 234, 236 in the main shaft coupling fitting 168A, as well as the support bearing 170A disposed in the recess 236.

Figure 19:
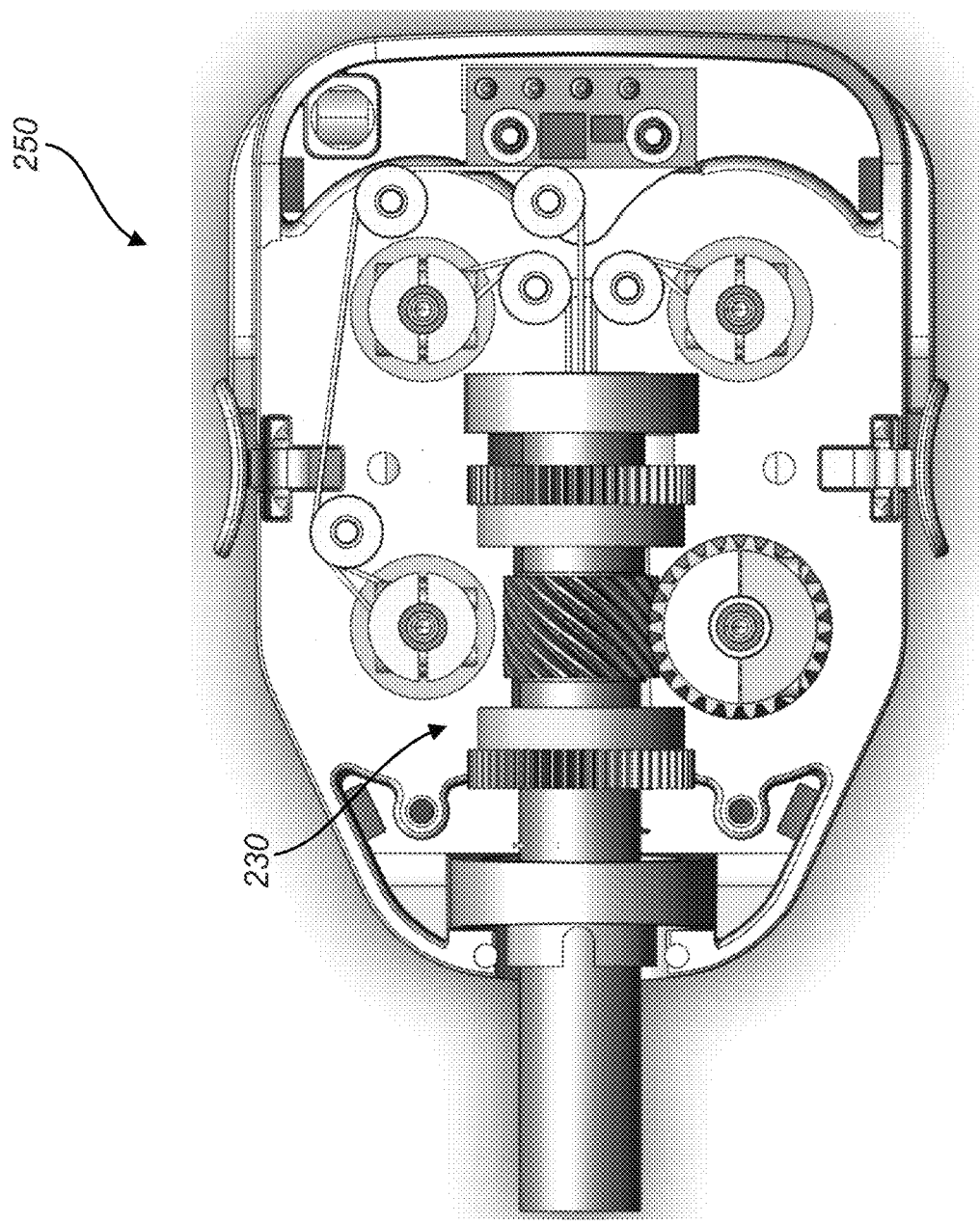
FIG. 19 is a plan view illustration of the integration of the actuation assembly of FIG. 16 within a proximal tool chassis, in accordance with many embodiments.

FIG. 19 is a plan view illustration of the integration of the actuation assembly 230 within a proximal tool chassis 250, in accordance with many embodiments. In addition to supporting and actuating the actuation assembly 230, the proximal tool chassis 250 further includes actuation and routing components for three pairs of control cables that are routed within the rotatable main shaft.

Figure 20:
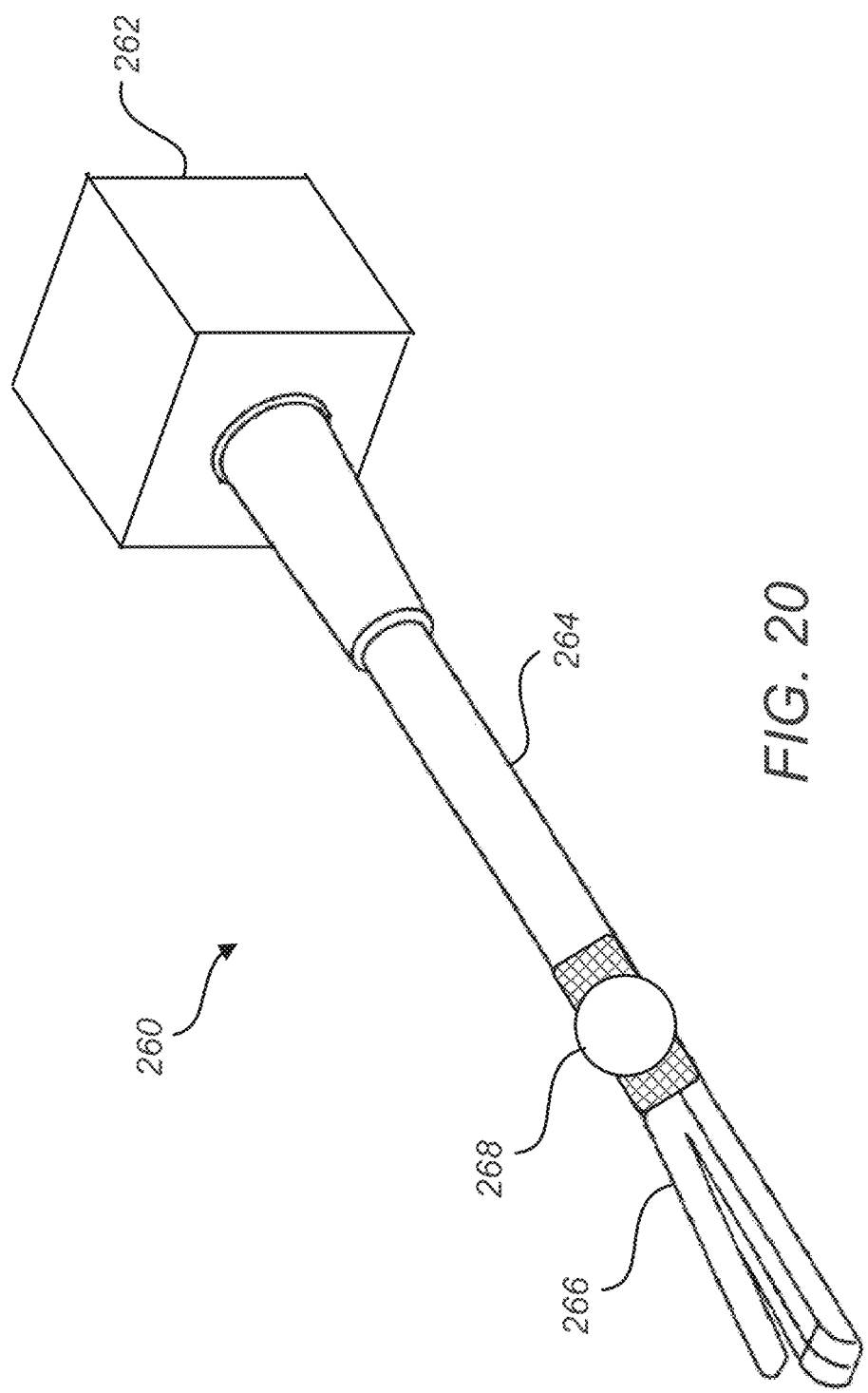
FIG. 20 is a simplified diagrammatic illustration of a surgical assembly, in accordance with many embodiments.

FIG. 20 is a simplified perspective view diagrammatic illustration of a surgical assembly 260, in accordance with many embodiments. The surgical assembly 260 includes a proximal actuation mechanism 262, a rotatable main shaft 264, an end effector 266, and a wrist mechanism 268. The end effector 266 can include one or more shaft driven mechanisms (e.g., a clamping mechanism, a linear cutting mechanism, a stapling mechanism). The surgical assembly 260 can also include one or more cable actuated mechanisms, for example, a cable actuation mechanism that articulates a base of the end effector relative to the main shaft via the wrist mechanism 268, and/or a cable actuation mechanism that articulates a portion of the end effector relative to the end effector base. The proximal actuation mechanism 262 can include the above discussed actuation mechanism for the mounting and actuation of one or more offset drive shafts routed within the rotatable main shaft 264. The proximal actuation mechanism 262 can be configured for use in a variety of applications, for example, as a hand held device with manual and/or automated actuation for the rotation of the main shaft 264 and/or the one or more internal drive shafts. As such, the surgical assembly 260 can have applications beyond minimally invasive robotic surgery, for example, non-robotic minimally invasive surgery, non-minimally invasive robotic surgery, non-robotic non-minimally invasive surgery, as well as other applications where the use of one or more offset drive shafts within a rotatable outer shaft would be beneficial.

Figure 21:
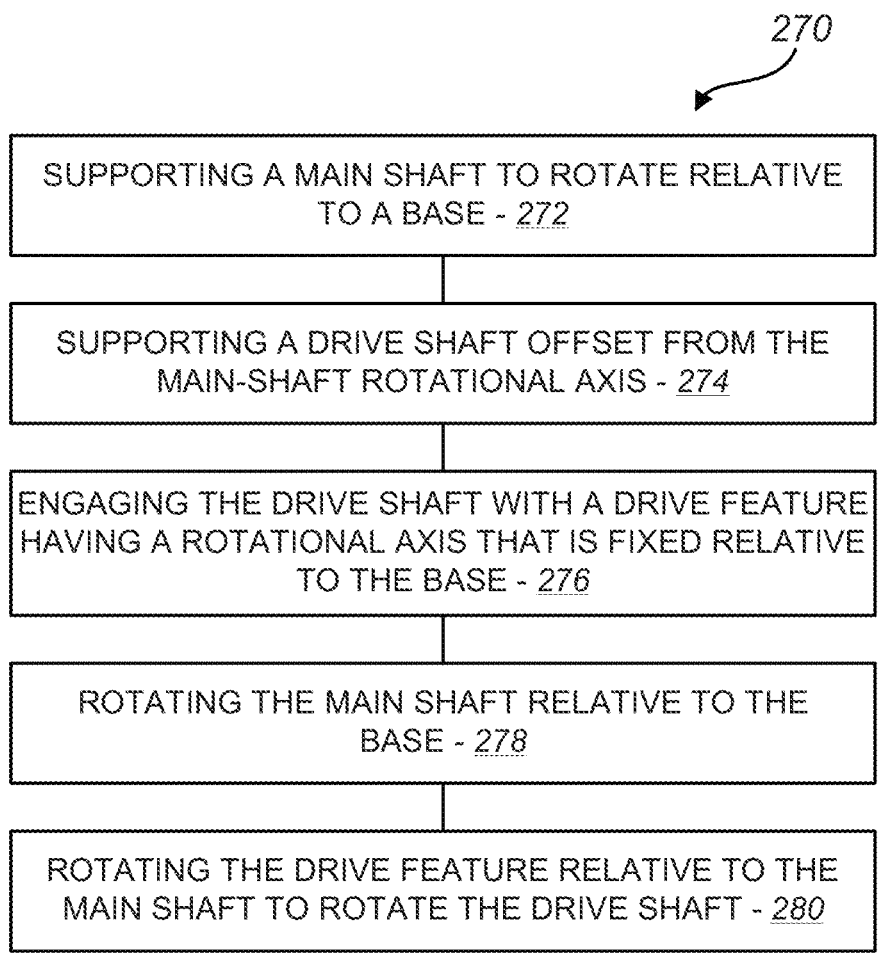
FIG. 21 is a flow diagram of a method for transmitting torque through an offset drive shaft routed within a rotatable main shaft, in accordance with many embodiments.

FIG. 21 is a simplified flow diagram of a method 270 for transmitting torque through an offset drive shaft routed within a rotatable main shaft, in accordance with many embodiments. In step 272, a main shaft is supported to rotate relative to a base. In step 274, a drive shaft is supported to rotate relative to the main shaft about a drive shaft rotational axis that is offset from the main shaft rotational axis. In step 276, the offset drive shaft is engaged with a drive feature having a rotational axis that is fixed relative to the base. In step 278, the main shaft is rotated relative to the base. In step 280, the drive shaft is rotated relative to the main shaft by rotating the drive feature relative to the main shaft. The steps of method 270 can be accomplished, for example, using the embodiments discussed above with respect to FIG. 6 through FIG. 19.

Figure 22:
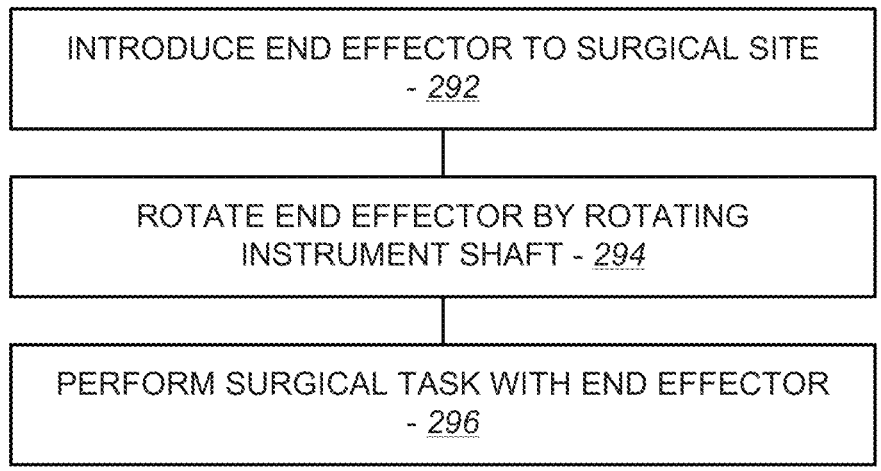
FIG. 22 is a flow diagram of a minimally invasive surgical method, in accordance with many embodiments.

FIG. 22 is a simplified flow diagram of a minimally invasive surgical method 290, in accordance with many embodiments. In step 292, an end effector of a surgical tool is introduced to a surgical site, for example, an internal surgical site via a minimally invasive aperture or natural body orifice. The end effector is mounted to a distal end of an elongated instrument shaft mounted to rotate relative to a base so that the end effector can be rotated with the instrument shaft relative to the base. The end effector is operatively coupled with a first drive shaft so that rotating the first drive shaft relative to the instrument shaft actuates an end effector first mechanism, the first drive shaft being mounted to rotate relative to the instrument shaft about a first drive shaft rotational axis that is offset from the instrument shaft rotational axis. In step 294, the end effector is rotated by rotating the instrument shaft. In step 296, a surgical task is performed with the end effector by actuating the end effector first mechanism.

In many embodiments, the method 290 involves the use of an end effector that is actuated by two drive shafts. A wide range of end effector mechanisms can be drive shaft actuated. For example, the end effector can include a clamping feature actuated by the first drive shaft. The end effector can include a movable cutting feature actuated by the second drive shaft. The surgical task can include clamping tissue with the clamping feature and cutting tissue with the movable cutting feature. The second drive shaft can be mounted to rotate relative to the instrument shaft about a second drive shaft rotational axis that is offset from the instrument shaft rotational axis. The end effector can include a cutting and stapling device actuated by the second drive shaft. The surgical task can include clamping tissue with the clamping feature, stapling tissue with the cutting and stapling device, and cutting tissue with the cutting and stapling device.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A minimally invasive surgical method comprising:
introducing an end effector to an internal surgical site within a patient through a minimally invasive aperture or natural orifice by manipulating an instrument shaft, wherein the end effector comprises an end effector base that is coupled to the instrument shaft via a wrist, wherein the instrument shaft has a proximal end and a distal end, and wherein an instrument shaft center axis extends through the proximal end and the distal end;
operating an end effector articulation mechanism to reorient the end effector base relative to the instrument shaft; and
performing a first surgical task with the end effector by operating a first drive shaft motor to rotate a first drive shaft relative to the instrument shaft so that the first drive shaft actuates a first actuated mechanism of the end effector, wherein the first drive shaft is rotated relative to the instrument shaft around a first drive shaft axis that is offset from the instrument shaft center axis.

2. The method of claim 1, further comprising:
outputting, by a first encoder coupled to the first drive shaft motor, a first drive shaft motor position signal to a controller; and
controlling, by the controller based on the first drive shaft motor position signal, operation of the first drive shaft motor in response to control signals from an input device.

3. The method of claim 1, further comprising operating a main shaft motor to rotate the instrument shaft relative to a proximal tool chassis around the instrument shaft center axis to rotate the end effector base relative to the patient.

4. The method of claim 3, further comprising:
outputting, by a main shaft encoder coupled to the main shaft motor, a main shaft motor position signal to a controller;
controlling, by the controller based on the main shaft motor position signal, operation of the main shaft motor in response to control signals from an input device.

5. The method of claim 4, further comprising:
outputting, by a first encoder coupled to the first drive shaft motor, a first drive shaft motor position signal to the controller; and
controlling, by the controller based on the first drive shaft motor position signal, operation of the first drive shaft motor in response to control signals from an input device.

6. The method of claim 3, wherein rotating the first drive shaft relative to the instrument shaft comprises:
engaging the first drive shaft with a first drive feature having a first drive feature rotational axis that is fixed relative to the proximal tool chassis; and
rotating the first drive feature relative to the instrument shaft so as to rotate the first drive shaft relative to the instrument shaft.

7. The method of claim 6, wherein the first drive feature comprises a first internal ring gear engaged with first external gear teeth that extend through a first opening in the instrument shaft and are drivingly coupled with the first drive shaft.

8. The method of claim 7, wherein the first drive feature rotational axis is coincident with the instrument shaft center axis.

9. The method of claim 1, wherein:
the wrist is configured for reorientation of the end effector base relative to the instrument shaft about two axes; and
operating the end effector articulation mechanism to reorient the end effector base relative to the instrument shaft comprises operating a first control cable motor to actuate a first pair of control cables coupled with the end effector base.

10. The method of claim 9, wherein operating the end effector articulation mechanism to reorient the end effector base relative to the instrument shaft further comprises operating a second control cable motor to actuate a second pair of control cables coupled with the end effector base.

11. The method of claim 10, further comprising:
outputting, by a first control cable motor encoder coupled to the first control cable motor, a first control cable motor position signal to a controller;
controlling, by the controller based on the first control cable motor position signal, operation of the first control cable motor in response to control signals from an input device;
outputting, by a second control cable motor encoder coupled to the second control cable motor, a second control cable motor position signal to the controller; and
controlling, by the controller based on the second control cable motor position signal, operation of the second control cable motor in response to control signals from the input device.

12. The method of claim 1, further comprising operating a jaw control cable motor to actuate a pair of control cables coupled with a jaw of the end effector to articulate the jaw relative to the end effector base.

13. The method of claim 12, further comprising:
outputting, by a jaw control cable motor encoder coupled to the jaw control cable motor, a jaw control cable motor position signal to a controller; and
controlling, by the controller based on the jaw control cable motor position signal, operation of the jaw control cable motor in response to control signals from an input device.

14. The method of claim 1, wherein the first actuated mechanism of the end effector comprises a tissue stapling device.

15. The method of claim 1, further comprising operating a second drive shaft motor to rotate a second drive shaft relative to the instrument shaft so that the second drive shaft actuates a second actuated mechanism of the end effector, wherein the second drive shaft is rotated relative to the instrument shaft around a second drive shaft axis that is offset from the instrument shaft center axis.

16. The method of claim 15, further comprising:
outputting, by a first encoder coupled to the first drive shaft motor, a first drive shaft motor position signal to a controller;
controlling, by the controller based on the first drive shaft motor position signal, operation of the first drive shaft motor in response to control signals from an input device;
outputting, by a second encoder coupled to the second drive shaft motor, a second drive shaft motor position signal to the controller; and
controlling, by the controller based on the second drive shaft motor position signal, operation of the second drive shaft motor in response to control signals from the input device.

17. The method of claim 15, wherein rotating the second drive shaft relative to the instrument shaft comprises:
engaging the second drive shaft with a second drive feature having a second drive feature rotational axis; and
rotating the second drive feature relative to the instrument shaft so as to rotate the second drive shaft relative to the instrument shaft.

18. The method of claim 17, wherein the second drive feature comprises a second internal ring gear engaged with second external gear teeth that extend through a second opening in the instrument shaft and are drivingly coupled with the second drive shaft.

19. The method of claim 18, wherein the second drive feature rotational axis is coincident with the instrument shaft center axis.

20. The method of claim 15, wherein the second actuated mechanism of the end effector actuates a tissue clamping feature of the end effector.

* * * * *

UNITED STATES PATENT AND TRADEMARK OFFICE
CERTIFICATE OF CORRECTION

| | | |
|---|---|---|
| PATENT NO. | : 11,660,152 B2 | Page 1 of 1 |
| APPLICATION NO. | : 16/998838 | |
| DATED | : May 30, 2023 | |
| INVENTOR(S) | : Gregory W. Dachs et al. | |

It is certified that error appears in the above-identified patent and that said Letters Patent is hereby corrected as shown below:

On the Title Page

In Related U.S. Application Data:
Please delete "15/677,752" and insert --15/677,782--.

Signed and Sealed this
Twentieth Day of February, 2024

Katherine Kelly Vidal
*Director of the United States Patent and Trademark Office*